(12) United States Patent
Finsinger et al.

(10) Patent No.: US 7,598,274 B2
(45) Date of Patent: Oct. 6, 2009

(54) PYRROLE DERIVATIVES

(75) Inventors: Dirk Finsinger, Darmstadt (DE); Hans-Peter Buchstaller, Griesheim (DE); Lars Burgdorf, Frankfurt am Main (DE); Matthias Wiesner, Seeheim-Jugenheim (DE); Christiane Amendt, Darmstadt (DE); Matthias Grell, Darmstadt (DE); Christian Sirrenberg, Darmstadt (DE); Frank Zenke, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 465 days.

(21) Appl. No.: 10/579,825

(22) PCT Filed: Oct. 26, 2004

(86) PCT No.: PCT/EP2004/012076

§ 371 (c)(1),
(2), (4) Date: May 17, 2006

(87) PCT Pub. No.: WO2005/049603

PCT Pub. Date: Jun. 2, 2005

(65) Prior Publication Data

US 2007/0149594 A1    Jun. 28, 2007

(30) Foreign Application Priority Data

Nov. 19, 2003   (DE) ................ 103 54 060

(51) Int. Cl.
*A61K 31/4439*   (2006.01)
*C07D 401/02*    (2006.01)

(52) U.S. Cl. .................... 514/343; 546/279.1

(58) Field of Classification Search ........ 514/408, 514/423, 343; 546/279.1; 548/537, 561
See application file for complete search history.

(56) References Cited

U.S. PATENT DOCUMENTS

2004/0138269 A1    7/2004  Sun et al.
2004/0254186 A1   12/2004  Dean et al.
2008/0234270 A1*   9/2008  Bannen et al. ........... 514/235.5

FOREIGN PATENT DOCUMENTS

WO    WO 03022833    3/2003

OTHER PUBLICATIONS

Vippagunta et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*

* cited by examiner

*Primary Examiner*—Kamal A Saeed
*Assistant Examiner*—Kristin Bianchi
(74) *Attorney, Agent, or Firm*—Millen, White, Zelano, Branigan, P.C.

(57) ABSTRACT

Compounds of the formula (I), in which X, Y, Z and Ar have the meanings indicated in claim 1, are inhibitors of Raf kinase and can be employed, inter alia, for the treatment of tumours

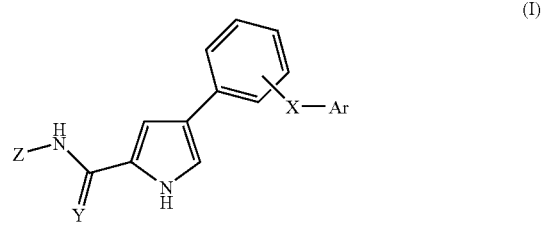

24 Claims, No Drawings

PYRROLE DERIVATIVES

BACKGROUND OF THE INVENTION

The invention had the object of finding novel compounds having valuable properties, in particular those which can be used for the preparation of medicaments.

The present invention relates to compounds and to the use of compounds in which the inhibition, regulation and/or modulation of kinase signal transduction, in particular by serine/threonine kinases, plays a role, further-more to pharmaceutical compositions which comprise these compounds, and to the use of the compounds for the treatment of kinase-induced diseases.

The invention relates to the compounds of the formula I as inhibitors of Raf kinases.

Protein phosphorylation is a fundamental process for the regulation of cellular functions. The coordinated action of both protein kinases and phosphatases controls the degrees of phosphorylation and, hence, the activity of specific target proteins. One of the predominant roles of protein phosphorylation is in signal transduction, where extracellular signals are amplified and propagated by a cascade of protein phosphorylation and dephosphorylation events, for example in the $p21^{ras}$/Raf pathway.

The $p21^{ras}$ gene was discovered as an oncogene of the Harvey (H-Ras) and Kirsten (K-Ras) rat sarcoma viruses. In humans, characteristic mutations in the cellular Ras gene (c-Ras) have been associated with many different types of cancer. These mutant alleles, which render Ras constitutively active, have been shown to transform cells, such as, for example, the murine cell line NIH 3T3, in culture.

The $p21^{ras}$ oncogene is a major contributor to the development and progression of human solid carcinomas and is mutated in 30% of all human carcinomas (Bolton et al. (1994) Ann. Rep. Med. Chem., 29, 165-74; Bos. (1989) Cancer Res., 49, 4682-9). In its normal, unmutated form, the Ras protein is a key element of the signal transduction cascade directed by growth factor receptors in almost all tissues (Avruch et al. (1994) Trends Biochem. Sci., 19, 279-83).

Biochemically, Ras is a guanine nucleotide binding protein, and cycling between a GTP-bound activated and a GDP-bound resting form is strictly controlled by Ras endogenous GTPase activity and other regulatory proteins. The Ras gene product binds to guanine triphosphate (GTP) and guanine diphosphate (GDP) and hydrolyses GTP to GDP. Ras is active in the GTP-bound state. In the Ras mutants in cancer cells, the endogenous GTPase activity is reduced and the protein consequently transmits constitutive growth signals to downstream effectors, such as, for example, the enzyme Raf kinase. This leads to the cancerous growth of the cells which carry these mutants (Magnuson et al. (1994) Semin. Cancer Biol., 5, 247-53). The Ras proto-oncogene requires a functionally intact C-Raf-1 proto-oncogene in order to transduce growth and differentiation signals initiated by receptor- and non-receptor-type tyrosine kinases in higher eukaryotes.

Activated Ras is necessary for the activation of the C-Raf-1 proto-onco-gene, but the biochemical steps through which Ras activates the Raf-1 protein (Ser/Thr) kinase are now well characterised. It has been shown that inhibiting the effect of active Ras by inhibiting the Raf kinase signalling pathway by administration of deactivating antibodies to Raf kinase or by co-expression of dominant negative Raf kinase or dominant negative MEK (MAPKK), the substrate of Raf kinase, leads to reversion of transformed cells to the normal growth phenotype, see: Daum et al. (1994) Trends Biochem. Sci., 19, 474-80; Fridman et al. (1994) J. Biol. Chem., 269, 30105-8. Kolch et al. (1991) Nature, 349, 426-28) and for a review Weinstein-Oppenheimer et al. Pharm. & Therap. (2000), 88, 229-279.

Similarly, inhibition of Raf kinase (by antisense oligodeoxynucleotides) has been correlated in vitro and in vivo with inhibition of the growth of a variety of human tumour types (Monia et al., Nat. Med. 1996, 2, 668-75); Geiger et al. (1997), Clin. Cancer Res. 3(7):1179-85; Lau et al. (2002), Antisense Nucl. Acid. Drug Dev. 12(1): 11-20; Mc Phillips et al. (2001), Br. J. Cancer 85(11): 1754-8).

Raf serine- and threonine-specific protein kinases are cytosolic enzymes that stimulate cell growth in a variety of cellular systems (Rapp, U. R., et al. (1988) in The Oncogene Handbook; T. Curran, E. P. Reddy and A. Skalka (eds.) Elsevier Science Publishers; The Netherlands, pp. 213-253; Rapp, U. R., et al. (1988) Cold Spring Harbor Sym. Quant. Biol. 53:173-184; Rapp, U. R., et al. (1990) Inv Curr. Top. Microbiol. Immunol. Potter and Melchers (eds.), Berlin, Springer-Verlag 166:129-139).

Three isozymes have been characterised:

C-Raf (Raf-1) (Bonner, T. I., et al. (1986) Nucleic Acids Res. 14:1009-1015). A-Raf (Beck, T. W., et al. (1987) Nucleic Acids Res. 15:595-609), and B-Raf (Qkawa, S., et al. (1998) Mol. Cell. Biol. 8:2651-2654; Sithanandam, G. et al. (1990) Oncogene:1775). These enzymes differ in their expression in various tissues. Raf-1 is expressed in all organs and in all cell lines that have been examined, and A- and B-Raf are expressed in urogenital and brain tissues respectively (Storm, S. M. (1990) Oncogene 5:345-351).

Raf genes are proto-oncogenes: they can initiate malignant transformation of cells when expressed in specifically altered forms. Genetic changes that lead to oncogenic activation generate a constitutively active protein kinase by removal of or interference with an N-terminal negative regulatory domain of the protein (Heidecker, G., et al. (1990) Mol. Cell. Biol. 10:2503-2512; Rapp, U. R., et al. (1987) in Oncogenes and Cancer; S. A. Aaronson, J. Bishop, T. Sugimura, M. Terada, K. Toyoshima and P. K. Vogt (eds.) Japan Scientific Press, Tokyo). Microinjection into NIH 3T3 cells of oncogenically activated, but not wild-type, versions of the Raf protein prepared with *Escherichia coli* expression vectors results in morphological transformation and stimulates DNA synthesis (Rapp, U. R., et al. (1987) in Oncogenes and Cancer; S. A. Aaronson, J. Bishop, T. Sugimura, M. Terada, K. Toyoshima, and P. K. Vogt (eds.) Japan Scientific Press, Tokyo; Smith, M. R., et al. (1990) Mol. Cell. Biol. 10:3828-3833).

Activating mutants of B-Raf have been identified in various types of human cancer, for example of the intestine, the ovaries, melanomas and sarco-mas (Davies, H. et al. (2002), Nature 417, 949-945; published online 9 Jun. 2002, 10.1038/nature00766). The predominant mutation is a single phosphomimetic substitution in the kinase activation domain (V599E), which results in constitutive kinase activity and transformation of NIH3T3 cells.

The process of angiogenesis is the development of new blood vessels, generally capillaries, from pre-existing vasculature. Angiogenesis is defined as involving (i) activation of endothelial cells; (ii) increased vascular permeability; (iii) subsequent dissolution of the basement membrane and extravisation of plasma components leading to formation of a provisional fibrin gel extracellular matrix; (iv) proliferation and mobilisation of endothelial cells; (v) reorganisation of mobilised endothelial cells to form functional capillaries; (vi) capillary loop formation; and (vii) deposition of basement membrane and recruitment of perivascular cells to newly formed vessels.

Normal angiogenesis is activated during tissue growth, from embryonic development through maturity, and then enters a period of relative quiescence during adulthood.

Normal angiogensesis is also activated during wound healing and at certain stages of the female reproductive cycle. Inappropriate or pathological angiogenesis has been associated with several conditions, including various retinopathies; ischemic disease; atherosclerosis; chronic inflammatory disorders; rheumatoid arthritis, and cancer. The role of angiogenesis in conditions is discussed, for instance, in Fan et al, Trends in Pharmacol Sci. 16:54 66; Shawver et al, DOT Vol. 2, No. 2 Feb. 1997; Folkmann, 1995, Nature Medicine 1:27-31.

In cancer, the growth of solid tumors has been shown to be angiogenesis-dependent. (see Folkmann, J., J. Nat'l. Cancer Inst., 1990, 82, 4-6.) Consequently, the targeting of pro-angiogenic pathways is a strategy being widely pursued in order to provide new therapeutics in these areas of great, unmet medical need.

Raf is involved in angiogenic processes. Endothelial growth factors (for example vascular endothelial growth factor VEGF or basic fibroblast growth factor bFGF) activate receptor tyrosine kinases (for example VEGFR-2) and signal through the Ras/Raf/Mek/Erk kinase cascade and protect endothelial cells against apoptosis (Alavi et al. (2003), Science 301, 94-96; Hood, J. D. et al. (2002), Science 296, 2404; Mikula, M. et al. (2001), EMBO J. 20, 1952; Hauser, M. et al. (2001), EMBO J. 20, 1940; Wojnowski et al. (1997), Nature Genet. 16, 293). Activation of VEGFR-2 by VEGF is a critical step in the signal transduction pathway that initiates tumor angiogenesis. VEGF expression may be constitutive to tumour cells and can also be upregulated in response to certain stimuli. One such stimulus is hypoxia, where VEGF expression is upregulated in both tumour and associated host tissues. The VEGF ligand activates VEGFR-2 by binding to its extracellular VEGF binding site. This leads to receptor dimerisation of VEGFRs and autophosphorylation of tyrosine residues at the intracellular kinase domain of VEGFR-2. The kinase domain causes a transfer of a phosphate from ATP to the tyrosine residues, thus providing binding sites for signalling proteins downstream of VEGFR-2, ultimately leading to initiation of angiogenesis (McMahon, G., The Oncologist, Vol. 5, No. 90001, 3-10, April 2000).

Mice with a targeted disruption in the B-Raf gene die of vascular defects during development (Wojnowski, L. et al. 1997, Nature Genetics 16, page 293-296). These mice show defects in the formation of the vascular sys-tem and in angiogenesis, for example enlarged blood vessels and increased apoptotic death of differentiated endothelial cells.

Consequently, activated Raf-1 is an intracellular activator of cell growth. Raf-1 protein serine kinase is a candidate for the downstream effector of mitogen signal transduction, since Raf oncogenes overcome growth arrest resulting from a block of cellular Ras activity due either to a cellular mutation (Ras revertant cells) or microinjection of anti-Ras antibodies (Rapp, U. R., et al. (1988) in The Oncogene Handbook, T. Curran, E. P. Reddy and A. Skalka (eds.), Elsevier Science Publishers; The Netherlands, pp. 213-253; Smith, M. R., et al. (1986) Nature (London) 320:540-543).

C-Raf function is required for transformation by a variety of membrane-bound oncogenes and for growth stimulation by mitogens contained in serums (Smith, M. R., et al. (1986) Nature (London) 320:540-543). Raf-1 protein serine kinase activity is regulated by mitogens via phosphorylation (Morrison, D. K., et al. (1989) Cell 58:648-657), which also effects sub-cellular distribution (Olah, Z., et al. (1991) Exp. Brain Res. 84:403; Rapp, U. R., et al. (1988) Cold Spring Harbor Sym. Quant. Biol. 53:173-184. Raf-1 activating growth factors include platelet-derived growth factor (PDGF) (Morrison, D. K., et al. (1988) Proc. Natl. Acad. Sci. USA 85:8855-8859), colony-stimulating factor (Baccarini, M., et al. (1990) EMBO J. 9:3649-3657), insulin (Blackshear, P. J., et al. (1990) J. Biol. Chem. 265:12115-12118), epidermal growth factor (EGF) (Morrison, R. K., et al. (1988) Proc. Natl. Acad. Sci. USA 85:8855-8859), interleukin-2 (Turner, B. C., et al. (1991) Proc. Natl. Acad. Sci. USA 88:1227) and interleukin-3 and granulocyte macrophage colony-stimulating factor (Carroll, M. P., et al. (1990) J. Biol. Chem. 265:19812-19817).

After mitogen treatment of cells, the transiently activated Raf-1 protein serine kinase translocates to the perinuclear area and the nucleus (Olah, Z., et al. (1991) Exp. Brain Res. 84:403; Rapp, U. R., et al. (1988) Cold Spring Harbor Sym. Quant. Biol. 53:173-184). Cells containing activated Raf are altered in their pattern of gene expression (Heidecker, G., et al. (1989) in Genes and signal transduction in multistage carcinogenesis, N. Colburn (ed.), Marcel Dekker, Inc., New York, pp. 339-374) and Raf onco-genes activate transcription from Ap-I/PEA3-dependent promoters in transient transfection assays (Jamal, S., et al. (1990) Science 344:463-466; Kaibuchi, K., et al. (1989) J. Biol. Chem. 264:20855-20858; Wasylyk, C., et al. (1989) Mol. Cell. Biol. 9:2247-2250).

There are at least two independent pathways for Raf-1 activation by extracellular mitogens: one involving protein kinase C (KC) and a second initiated by protein tyrosine kinases (Blackshear, P. J., et al. (1990) J. Biol. Chem. 265: 12131-12134; Kovacina, K. S., et al. (1990) J. Biol. Chem. 265:12115-12118; Morrison, D. K., et al. (1988) Proc. Natl. Acad. Sci. USA 85:8855-8859; Siegel, J. N., et al. (1990) J. Biol. Chem. 265:18472-18480; Turner, B. C., et al. (1991) Proc. Natl. Acad. Sci. USA 88:1227). In each case, activation involves Raf-1 protein phosphorylation. Raf-1 phosphorylation may be a consequence of a kinase cascade amplified by autophosphorylation or may be caused entirely by autophosphorylation initiated by binding of a putative activating ligand to the Raf-1 regulatory domain, analogous to PKC activation by diacylglycerol (Nishizuka, Y. (1986) Science 233:305-312).

One of the principal mechanisms by which cellular regulation is effected is through the transduction of extracellular signals across the membrane that in turn modulate biochemical pathways within the cell. Protein phosphorylation represents one course by which intracellular signals are propagated from molecule to molecule resulting finally in a cellular response. These signal transduction cascades are highly regulated and often overlap, as is evident from the existence of many protein kinases as well as phosphatases. Phosphorylation of proteins occurs predominantly at serine, threonine or tyrosine residues, and protein kinases have therefore been classified by their specificity of phosphorylation site, i.e. serine/threonine kinases and tyrosine kinases. Since phosphorylation is such a ubiquitous process within cells and since cellular phenotypes are largely influenced by the activity of these pathways, it is currently believed that a number of conditions and/or diseases are attributable to either aberrant activation or functional mutations in the molecular components of kinase cascades. Consequently, considerable attention has been devoted to the characterisation of these proteins and compounds that are able to modulate their activity (review article see: Weinstein-Oppenheimer et al. Pharma. &. Therap., 2000, 88, 229-279).

The synthesis of small compounds which specifically inhibit, regulate and/or modulate signal transduction by Raf kinases is therefore desirable and an aim of the present invention.

It has been found that the compounds according to the invention and salts thereof have very valuable pharmacological properties while being well tolerated.

In particular, they exhibit tyrosine kinase inhibiting properties.

It has furthermore been found that the compounds according to the invention are inhibitors of the enzyme Raf kinase. Since the enzyme is a down-stream effector of $p21^{ras}$, the inhibitors prove to be suitable in pharmaceutical compositions for use in human or veterinary medicine where inhibition of the Raf kinase pathway is indicated, for example in the treatment of tumours and/or cancerous cell growth mediated by Raf kinase. In particular, the compounds are suitable for the treatment of human and animal solid cancers, for example murine cancer, since the progression of these cancers is dependent upon the Ras protein signal transduction cascade and therefore susceptible to treatment by interruption of the cascade, i.e. by inhibiting Raf kinase. Accordingly, the compound according to the invention or a pharmaceutically acceptable salt thereof is administered for the treatment of diseases mediated by the Raf kinase pathway, especially cancer, including solid cancers, such as, for example, carcinomas (for example of the lungs, pancreas, thyroid, bladder or colon), myeloid diseases (for example myeloid leukaemia) or adenomas (for example villous colon adenoma), pathological angiogenesis and metastatic cell migration. The compounds are furthermore suitable for the treatment of complement activation dependent chronic inflammation (Niculescu et al. (2002) Immunol. Res., 24:191-199) and HIV-1 (human immunodeficiency virus type 1) induced immunodeficiency (Popik et al. (1998) J Virol, 72: 6406-6413), infection disease, influenza A virus (Pleschka, S. et al. (2001), Nat. Cell. Biol., 3(3):301-5) and *Heliobacter pylori* infection (Wessler, S. et al. (2002), FASEB J., 16(3): 417-9).

Surprisingly, it has been found that compounds according to the invention are able to interact with signalling pathways, especially the signalling pathways described herein and preferably the Raf kinase signalling pathway. The compounds according to the invention preferably exhibit an advantageous biological activity which can easily be demonstrated in enzyme-based assays, for example assays as described herein. In such enzyme-based assays, the compounds according to the invention preferably exhibit and cause an inhibiting effect, which is usually documented by $IC_{50}$ values in a suitable range, preferably in the micromolar range and more preferably in the nanomolar range.

As discussed herein, these signalling pathways are relevant for various diseases. Accordingly, the compounds according to the invention are suit-able for the prophylaxis and/or treatment of diseases that are dependent on the said signalling pathways by interacting with one or more of the said signalling pathways.

The present invention therefore relates to compounds according to the invention as promoters or inhibitors, preferably as inhibitors, of the signalling pathways described herein. The invention therefore preferably relates to compounds according to the invention as promoters or inhibitors, preferably as inhibitors, of the Raf kinase pathway. The invention therefore preferably relates to compounds according to the invention as promoters or inhibitors, preferably as inhibitors, of Raf kinase. The invention still more preferably relates to compounds according to the invention as promoters or inhibitors, preferably as inhibitors, of one or more Raf kinases selected from the group consisting of A-Raf, B-Raf and C-Raf-1. The invention particularly preferably relates to compounds according to the invention as promoters or inhibitors, preferably as inhibitors, of C-Raf-1.

The present invention furthermore relates to the use of one or more compounds according to the invention in the treatment and/or prophylaxis of diseases, preferably the diseases described herein, that are caused, mediated and/or propagated by Raf kinases and in particular diseases that are caused, mediated and/or propagated by Raf kinases selected from the group consisting of A-Raf, B-Raf and C-Raf-1. The diseases discussed here are usually divided into two groups, hyperproliferative and non-hyperproliferative diseases. In this connection, psoriasis, arthritis, inflammation, endometriosis, scarring, benign prostatic hyperplasia, immunological diseases, autoimmune diseases and immunodeficiency diseases are regarded as non-cancerous diseases, of which arthritis, inflammation, immunological diseases, autoimmune diseases and immunodeficiency diseases are usually regarded as non-hyperproliferative diseases. In this connection, brain cancer, lung cancer, squamous cell cancer, bladder cancer, gastric cancer, pancreatic cancer, hepatic cancer, renal cancer, colorectal cancer, breast cancer, head cancer, neck cancer, oesophageal cancer, gynaecological cancer, thyroid cancer, lymphomas, chronic leukaemia and acute leukaemia are to be regarded as cancerous diseases, all of which are usually regarded as hyperproliferative diseases. Especially cancerous cell growth and especially cancerous cell growth mediated by Raf kinase is a disease which is a target of the present invention. The pre-sent invention therefore relates to compounds according to the invention as medicaments and/or medicament active ingredients in the treatment and/or prophylaxis of the said diseases and to the use of compounds according to the invention for the preparation of a pharmaceutical for the treatment and/or prophylaxis of the said diseases as well as to a method for the treatment of the said diseases which comprises the administration of one or more compounds according to the invention to a patient in need of such an administration.

It can be shown that the compounds according to the invention have an antiproliferative action in vivo in a xenotransplant tumour model. The compounds according to the invention are administered to a patient having a hyperproliferative disease, for example to inhibit tumour growth, to reduce inflammation associated with a lymphoproliferative disease, to inhibit trans-plant rejection or neurological damage due to tissue repair, etc. The present compounds are suitable for prophylactic or therapeutic purposes. As used herein, the term "treatment" is used to refer to both prevention of diseases and treatment of pre-existing conditions. The prevention of proliferation is achieved by administration of the compounds according to the invention prior to the development of overt disease, for example to prevent the growth of tumours, prevent metastatic growth, diminish restenosis associated with cardiovascular surgery, etc. Alternatively, the compounds are used for the treatment of ongoing diseases by stabilising or improving the clinical symptoms of the patient.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow the active agents to induce cell death or to inhibit migration, usually between about one hour and one week. In vitro testing can be carried out using cultivated cells from a biopsy sample. The viable cells remaining after the treatment are then counted.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

For the identification of a signal transduction pathway and for detection of interactions between various signal transduction pathways, various scientists have developed suitable models or model systems, for example cell culture models (for example Khwaja et al., EMBO, 1997, 16, 2783-93) and models of transgenic animals (for example White et al., Oncogene, 2001; 20, 7064-7072). For the determination of certain stages in the signal transduction cascade, interacting compounds can be utilised in order to modulate the signal (for example Stephens et al., Biochemical J., 2000, 351, 95-105). The compounds according to the invention can also be used as reagents for testing kinase-dependent signal transduction pathways in animals and/or cell culture models or in the clinical diseases mentioned in this application.

Measurement of the kinase activity is a technique which is well known to the person skilled in the art. Generic test systems for the determination of the kinase activity using substrates, for example histone (for example Alessi et al., FEBS Lett. 1996, 399, 3, pages 333-338) or the basic myelin protein are described in the literature (for example Campos-González, R. and Glenney, Jr., J. R. 1992, J. Biol. Chem. 267, page 14535).

For the identification of kinase inhibitors, various assay systems are available, for example Walters et al., Nature Drug Discovery 2003, 2; 259-266). In scintillation proximity assay (Sorg et al., J. of Biomolecular Screening, 2002, 7, 11-19) and flashplate assay, the radioactive phosphorylation of a protein or peptide as substrate with γATP is measured. In the presence of an inhibitory compound, a decreased radioactive signal, or none at all, is detectable. Furthermore, homogeneous time-resolved fluorescence resonance energy transfer (HTR-FRET) and fluorescence polarisation (FP) technologies are suitable as assay methods (Sills et al., J. of Biomolecular Screening, 2002, 191-214).

Other non-radioactive ELISA assay methods use specific phospho-antibodies (phospho-ABs). The phospho-AB binds only the phosphorylated substrate. This binding can be detected by chemiluminescence using a second peroxidase-conjugated anti-sheep antibody (Ross et al., 2002, Biochem. J., 2002, 366.977-981).

There are many diseases associated with deregulation of cell proliferation and cell death (apoptosis). The conditions of interest include, but are not limited to, the following. The compounds according to the invention are suitable for the treatment of a variety of conditions where there is proliferation and/or migration of smooth muscle cells and/or inflammatory cells into the intimal layer of a vessel, resulting in restricted blood flow through that vessel, for example in the case of neointimal occlusive lesions. Occlusive graft vascular diseases of interest include atherosclerosis, graft coronary vascular disease after transplantation, vein graft stenosis, peri-anastomotic prosthetic restenosis, restenosis after angioplasty or stent placement, and the like.

PRIOR ART

SUMMARY OF THE INVENTION

The invention relates to compounds of the formula I

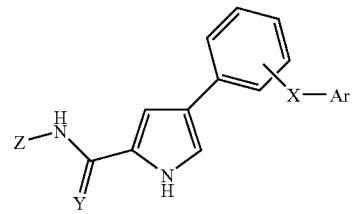

in which
Ar denotes phenyl, naphthyl, biphenyl or Het, each of which is unsubstituted or mono-, di-, tri-, tetra- or pentasubstituted by $R^1$,
X denotes —O—, —S—, —(CH$_2$)$_n$—, —C(=O)—, —CH(OH)—, —(CH$_2$)$_n$O—, —O(CH$_2$)$_n$—, —(CH$_2$)$_n$S—, —S(CH$_2$)$_n$—, —(CH$_2$)$_n$NH—, —NH(CH$_2$)$_n$—, —(CH$_2$)$_n$NA—, —NA(CH$_2$)$_n$—, —CHHal- or —C(Hal)$_2$-,
Y denotes O, S, CH—NO$_2$, C(CN)$_2$ or N—R$^4$,
Z denotes —Ar', —Ar'—X—Ar, —CH$_2$—Ar or —CH$_2$—Ar'—X—Ar,
Het denotes a mono- or bicyclic aromatic heterocycle having 1 to 4 N, O and/or S atoms,
$R^1$ denotes A, Ar', OR$^3$, SR$^3$, OAr', SAr', N(R$^3$)$_2$, NHAr', Hal, NO$_2$, CN, (CH$_2$)$_m$COOR$^3$, (CH$_2$)$_m$CON(R$^3$)$_2$, COR$^3$, S(O)$_m$A, S(O)$_m$Ar', NHCOA, NHCOAr', NHSO$_2$A, NHSO$_2$Ar', SO$_2$N(R$^3$)$_2$, —O—(CH$_2$)$_p$—NH$_2$, —O—(CH$_2$)$_p$—NHA, —O—(CH$_2$)$_p$—NA$_2$, —NH—(CH$_2$)$_p$—NH$_2$, —NH—(CH$_2$)$_p$—NHA, —NH—(CH$_2$)$_p$—NA$_2$, —NA-(CH$_2$)$_p$—NH$_2$, —NA-(CH$_2$)$_p$—NHA, —NA-(CH$_2$)$_p$—NA$_2$, —O—(CH$_2$)$_n$-Het$^1$ or Het$^1$,
$R^3$ denotes H, A or —(CH$_2$)$_n$Ar',
$R^4$ denotes H, CN, OH, A, (CH$_2$)$_m$Ar', COR$^3$, COAr', S(O)$_m$A or S(O)$_m$Ar',
Ar' denotes phenyl which is unsubstituted or mono-, di-, tri-, tetra- or pentasubstituted by A, Ph, OH, OA, SH, SA, OPh, SPh, NH$_2$, NHA, NA$_2$, NHPh, Hal, NO$_2$, CN, (CH$_2$)$_m$COOH, (CH$_2$)$_m$COOA, (CH$_2$)$_m$CONH$_2$, (CH$_2$)$_m$CONHA, CHO, COA, S(O)$_m$A, S(O)$_m$Ph, NHCOA, NHCOPh, NHSO$_2$A, NHSO$_2$Ph or SO$_2$NH$_2$,
Ph denotes phenyl which is unsubstituted or mono-, di- or trisubstituted by A, Hal, CN, COOR, COOH, NH$_2$, NO$_2$, OH or OA,
Het$^1$ denotes a monocyclic saturated heterocycle having 1 to 4 N, O and/or S atoms, which may be unsubstituted or mono-, di- or trisubstituted by Hal, A, OA, CN, (CH$_2$)$_n$OH, (CH$_2$)$_n$Hal, NH$_2$, =NH, =N—OH, =N—OA and/or carbonyl oxygen (=O),
A denotes alkyl having 1 to 10 C atoms, in which, in addition, 1-7H atoms may be replaced by F and/or chlorine,
Hal denotes F, Cl, Br or I,
n denotes 0, 1, 2 or 3,
m denotes 0, 1 or 2,
p denotes 1, 2, 3 or 4, and pharmaceutically usable derivatives, solvates, salts and stereoisomers thereof, including mixtures thereof in all ratios.

The invention also relates to the optically active forms (stereoisomers), the enantiomers, the racemates, the diastereomers and the hydrates and solvates of these compounds. The term solvates of the compounds is taken to mean adductions of inert solvent molecules onto the compounds which form owing to their mutual attractive force. Solvates are, for example, mono- or dihydrates or alkoxides.

The term pharmaceutically usable derivatives is taken to mean, for example, the salts of the compounds according to the invention and also so-called prodrug compounds.

The term prodrug derivatives is taken to mean compounds of the formula I which have been modified by means of, for example, alkyl or acyl groups, sugars or oligopeptides and which are rapidly cleaved in the organism to form the effective compounds according to the invention.

These also include biodegradable polymer derivatives of the compounds according to the invention, as described, for example, in Int. J. Pharm. 115, 61-67 (1995).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the progress of a disease, condition or disorder.

The expression "therapeutically effective amount" also encompasses the amounts which are effective for increasing normal physiological function.

The invention also relates to the use of mixtures of the compounds according to the invention, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

The invention relates to the compounds of the formula I and salts thereof and to a process for the preparation of compounds of the formula I according to claims 1-10 and pharmaceutically usable derivatives, salts, solvates, tautomers and stereoisomers thereof, characterised in that a) for the preparation of compounds of the formula I in which Y denotes O, a compound of the formula II

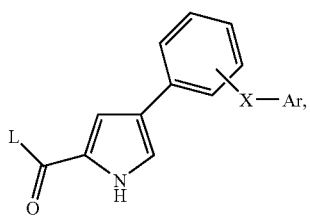

in which X and Ar have the meanings indicated in claim 1, and L denotes Cl, Br, I or a free or reactively functionally modified OH group, is reacted with a compound of the formula III

Z-NH$_2$     III in which Z has the meaning indicated in claim 1, and/or a base or acid of the formula I is converted into one of its salts.

Above and below, the radicals X, Y, Z and Ar have the meanings indicated for the formula I, unless expressly stated otherwise.

A denotes alkyl, is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethyl-propyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoro-ethyl. A also denotes cycloalkyl.

Cycloalkyl preferably denotes cyclopropyl, cyclobutyl, cyclopentyl, cyclo-hexyl or cycloheptyl.

Alkylene is preferably unbranched and preferably denotes methylene, ethylene, propylene, butylene or pentylene.

$R^1$ preferably denotes, for example, A, such as, for example, methyl or ethyl; Ar', such as, for example, phenyl, F—, Cl— or bromophenyl or tolyl; $OR^3$, such as, for example, hydroxyl, methoxy or ethoxy; $SR^3$, such as, for example, $SCH_3$; OAr', such as, for example, phenoxy; SAr', such as, for example, S-phenyl; $N(R^3)_2$, such as, for example, amino, methylamino, ethylamino, dimethylamino or diethylamino; NHAr', such as, for example, anilino; Hal, $NO_2$, CN, $(CH_2)_mCOOR^3$, such as, for example, carboxyl, methoxycarbonyl, methoxycarbonylmethyl or ethoxycarbonylethyl; $(CH_2)_mCON(R^3)_2$, such as, for example, aminocarbonyl, N-methylamino-carbonyl, aminocarbonylmethyl or dimethylaminoethyl; $COR^3$, such as, for example, formyl, acetyl or propionyl; $S(O)_mA$, such as, for example, methylsulfonyl; $S(O)_mAr'$, such as, for example, phenylsulfonyl; NHCOA, such as, for example, acetamino; NHCOAr', phenylcarbonylamino; $NHSO_2A$, such as, for example, methylsulfonylamino; $NHSO_2Ar'$, such as, for example, phenylsulfonylamino; $SO_2N(R^3)_2$, such as, for example, di-methylaminosulfonyl; —O—$(CH_2)_p$—$NH_2$, such as, for example, 2-aminoethoxy; —O—$(CH_2)_p$—NHA, such as, for example, 2-methylaminoethoxy; —O—$(CH_2)_p$—$NA_2$, such as, for example, 2-dimethylaminoethoxy; —NH—$(CH_2)_p$—$NH_2$, such as, for example, 2-aminoethylamino; —NH—$(CH_2)_p$—NHA, such as, for example, 2-methylaminoethylamino; —NH—$(CH_2)_p$—$NA_2$, such as, for example, 2-dimethylaminoethylamino; —NA-$(CH_2)_p$—$NH_2$, such as, for example, (2-aminoethyl)methylamino; —NA-$(CH_2)_p$—NHA, such as, for example, (2-methylaminoethyl)methylamino; —NA-$(CH_2)_p$—$NA_2$, such as, for example, (2-dimethylaminoethyl)methylamino; —O—$(CH_2)_n$—$Het^1$, such as, for example, 2-(pyrrolidin-1-yl)ethoxy, 2-(1-piperidin-1-yl)ethoxy, 2-(morpholin-4-yl)ethoxy, 2-(piperazin-1-yl)ethoxy, 2-(4-methylpiperazin-1-yl)ethoxy, 2-(1-methylpiperidin-4-yl)ethoxy, 2-(4-hydroxyethylpiperazin-1-yl)ethoxy or 2-(4-hydroxypiperidin-1-yl)ethoxy;

or $Het^1$, such as, for example, 1-pyrrolidinyl, 1-piperidinyl, 4-morpholinyl, 1-piperazinyl, 4-methylpiperazin-1-yl, 4-piperidinyl, 1-methylpiperidin-4-yl, 4-hydroxyethylpiperazin-1-yl, 4-hydroxypiperidin-1-yl.

Ar preferably denotes unsubstituted phenyl, furthermore phenyl which is mono-, di-, tri-, tetra- or pentasubstituted by A, Ph, OH, OA, SH, SA, OPh, SPh, $NH_2$, NHA, $NA_2$, NHPh, Hal, $NO_2$, CN, $(CH_2)_m COOH$, $(CH_2)_m COOA$, $(CH_2)_m CONH_2$, $(CH_2)_m CONHA$, CHO, COA, $S(O)_m A$, $S(O)_m Ph$, NHCOA, NHCOPh, $NHSO_2 A$, $NHSO_2 Ph$ or $SO_2 NH_2$, such as, for example, o-, m- or p-tolyl, biphenyl, o-, m- or p-hydroxyphenyl, o-, m- or p-methoxyphenyl, o-, m- or p-mercaptophenyl, o-, m- or p-phenoxyphenyl, o-, m- or p-anilino, o-, m- or p-methylaminophenyl, o-, m- or p-phenylaminophenyl, o-, m- or p-fluorophenyl, o-, m- or p-chlorophenyl, o-, m- or p-bromophenyl, o-, m- or p-nitrophenyl, o-, m- or p-cyanophenyl, o-, m- or p-carboxyphenyl, o-, m- or p-carboxymethylphenyl, o-, m- or p-methoxycarbonylphenyl, o-, m- or p-methoxycarbonylmethylphenyl, o-, m- or p-aminocarbonylphenyl, o-, m- or p-methylaminocarbonylphenyl, o-, m- or p-formylphenyl, o-, m- or p-acetylphenyl, o-, m- or p-methylsulfonylphenyl, o-, m- or p-methylcarbonyl-aminophenyl, o-, m- or p-methylsulfonylaminophenyl, o-, m- or p-aminosulfonylphenyl, furthermore preferably 2,3-, 2,4-, 2,5-, 2,6-, 3,4- or 3,5-di-fluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 2-amino-3-chloro-, 2-amino-4-chloro-, 2-amino-5-chloro- or 2-amino-6-chlorophenyl, 2-nitro-4-N,N-di-methylamino- or 3-nitro-4-N,N-dimethylaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chloro-phenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl or 3-fluoro-4-methoxyphenyl;

furthermore, preferably, irrespective of additional substitutions, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7- benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxa-diazol-5-yl.

Ar' preferably denotes, for example, unsubstituted phenyl, furthermore phenyl which is mono-, di-, tri-, tetra- or pentasubstituted by A, Ph, OH, OA, SH, SA, OPh, SPh, $NH_2$, NHA, $NA_2$, NHPh, Hal, $NO_2$, CN, $(CH_2)_m COOH$, $(CH_2)_m COOA$, $(CH_2)_m CONH_2$, $(CH_2)_m CONHA$, CHO, COA, $S(O)_m$ A, $S(O)_m Ph$, NHCOA, NHCOPh, $NHSO_2 A$, $NHSO_2 Ph$ or $SO_2 NH_2$, such as, for example, o-, m- or p-tolyl, biphenyl, o-, m- or p-hydroxyphenyl, o-, m- or p-methoxyphenyl, o-, m- or p-mercaptophenyl, o-, m- or p-phenoxyphenyl, o-, m- or p-anilino, o-, m- or p-methylaminophenyl, o-, m- or p-phenylaminophenyl, o-, m- or p-fluorophenyl, o-, m- or p-chlorophenyl, o-, m- or p-bromophenyl, o-, m- or p-nitrophenyl, o-, m- or p-cyanophenyl, o-, m- or p-carboxyphenyl, o-, m- or p-carboxymethylphenyl, o-, m- or p-methoxycarbonylphenyl, o-, m- or p-methoxycarbonylmethylphenyl, o-, m- or p-aminocarbonylphenyl, o-, m- or p-methylaminocarbonylphenyl, o-, m- or p-formylphenyl, o-, m- or p-acetylphenyl, o-, m- or p-methylsulfonyl-phenyl, o-, m- or p-methylcarbonylaminophenyl, o-, m- or p-methylsulfonyl-aminophenyl, o-, m- or p-aminosulfonylphenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethyl-aminophenyl, 2,3,4-, 2,3,5-, 2,3,6-, 2,4,6- or 3,4,5-trichlorophenyl, 2,4,6-tri-methoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxy-phenyl, 3-chloro-4-acetamidophenyl or 3-fluoro-4-methoxyphenyl.

Het preferably denotes, for example, 2- or 3-furyl, 2- or 3-thienyl, 1-, 2- or 3-pyrrolyl, 1-, 2,4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, furthermore preferably 1,3-benzodioxol-5-yl, 1,4-benzodioxan-6-yl, 2,1,3-benzothiadiazol-4- or -5-yl or 2,1,3-benzoxadiazol-5-yl.

The substituent $R^1$ for Het is particularly preferably methylaminocarbonyl.

In a further preferred embodiment, Het denotes a monocyclic saturated heterocycle having 1 to 3 N, O and/or S atoms, particular preference is given to pyridyl.

Unsubstituted $Het^1$ preferably denotes, for example, tetrahydro-2- or -3-furyl, 1,3-dioxolan-4-yl, tetrahydro-2- or -3-thienyl, tetrahydro-1-, -2- or -4-imidazolyl, pyrrolidinyl, piperidinyl, morpholinyl or piperazinyl.

$Het^1$ particularly preferably denotes a monocyclic saturated heterocycle having 1 to 2 N atoms, which may be unsubstituted or monosubstituted by A or $(CH_2)_n OH$.

$Het^1$ very particularly preferably denotes 1-pyrrolidinyl, 1-piperidinyl, 4-morpholinyl, 1-piperazinyl, 4-methylpiperazin-1-yl, 4-piperidinyl, 1-methylpiperidin-4-yl, 4-hydroxyethylpiperazin-1-yl, 4-hydroxypiperidin-1-yl, 2-oxopiperidin-1-yl, 2-oxopyrrolidin-1-yl, 5,5-dimethyl-2-oxopyrrolidin-1-yl or 3-oxomorpholin-4-yl.

Y particularly preferably denotes O.

Z preferably denotes Ar, particularly preferably phenyl which is unsubstituted or mono-, di-, tri-, tetra- or pentasubstituted by A, OH, OA, $NH_2$, NHA, $NA_2$, $—O—(CH_2)_p—NH_2$, $—O—(CH_2)_p—NHA$, $—O—(CH_2)_p—NA_2$, $—NH—(CH_2)_p—NH_2$, $—NH—(CH_2)_p—NHA$, $—NH—(CH_2)_p—$ $NA_2$, —NA-$(CH_2)_p$—$NH_2$, —NA-$(CH_2)_p$—NHA, —NA-$(CH_2)_p$—$NA_2$, —O—$(CH_2)_n$-$Het^1$, $Het^1$ or Hal.

In a further embodiment, Z denotes phenyl which is unsubstituted or mono-, di-, tri-, tetra- or pentasubstituted by $R^1$, -phenylene-X—Ar, for example phenylene-O-Het, —$CH_2$—Ar or —$CH_2$-phenylene-X—Ar, where Het denotes, for example, pyridyl which is unsubstituted or monosubstituted by $R^1$.

Hal preferably denotes F, Cl or Br, but also 1, particularly preferably F or Cl.

Throughout the invention, all radicals which occur more than once, such as, for example, $R^1$, may be identical or different, i.e. are independent of one another.

The compounds of the formula I may have one or more chiral centres and therefore occur in various stereoisomeric forms. The formula I encompasses all these forms.

Accordingly, the invention relates, in particular, to the compounds of the formula I in which at least one of the said radicals has one of the preferred meanings indicated above. Some preferred groups of compounds may be expressed by the following sub-formulae Ia to Ij, which conform to the formula I and in which the radicals not designated in greater detail have the meaning indicated for the formula I, but in which in Ia X denotes 0 or —$(CH_2)_n$—;

in Ib Ar denotes Het or phenyl, each of which is unsubstituted or mono-, di-, tri-, tetra- or pentasubstituted by $R^1$;

in Ic $R^1$ denotes A, OH, OA, $NH_2$, NHA, $NA_2$, Hal, $(CH_2)_m CONH_2$, $(CH_2)_m CONHA$, $(CH_2)_m CONA_2$, —O—$(CH_2)_p$—$NH_2$, —O—$(CH_2)_p$—NHA, —O—$(CH_2)_p$—$NA_2$, —NH—$(CH_2)_p$—$NH_2$, —NH—$(CH_2)_p$—NHA, —NH—$(CH_2)_p$—$NA_2$, —NA-$(CH_2)_p$—$NH_2$, —NA-$(CH_2)_p$—NHA, —NA-$(CH_2)_p$—$NA_2$, —O—$(CH_2)_n$-$Het^1$ or $Het^1$;

in Id Het denotes a monocyclic aromatic heterocycle having 1 to 3 N, O and/or S atoms;

in Ie Y denotes 0;

in If Z denotes —Ar;

in Ig Z denotes phenyl which is unsubstituted or mono-, di-, tri-, tetra- or pentasubstituted by A, OH, OA, $NH_2$, NHA, $NA_2$, —O—$(CH_2)_p$—$NH_2$, —O—$(CH_2)_p$—NHA, —O—$(CH_2)_p$—$NA_2$, —NH—$(CH_2)_p$—$NH_2$, —NH—$(CH_2)_p$—NHA, —NH—$(CH_2)_p$—$NA_2$, —NA-$(CH_2)_p$—$NH_2$, —NA-$(CH_2)_p$—NHA, —NA-$(CH_2)_p$—$NA_2$, —O—$(CH_2)_n$-$Het^1$, $Het^1$ or Hal;

in Ih X denotes O,

Ar denotes Het or phenyl, each of which is unsubstituted or mono-, di-, tri-, tetra- or pentasubstituted by $R^1$, $R^1$ denotes A, OH, OA, $NH_2$, NHA, $NA_2$, Hal, —O—$(CH_2)_p$—$NH_2$, —O—$(CH_2)_p$—NHA, —O—$(CH_2)_p$—$NA_2$, —NH—$(CH_2)_p$—$NH_2$, —NH—$(CH_2)_p$—NHA, —NH—$(CH_2)_p$—$NA_2$, —NA-$(CH_2)_p$—$NH_2$, —NA-$(CH_2)_p$—NHA, —NA-$(CH_2)_p$—$NA_2$, $(CH_2)_m CONH_2$, $(CH_2)_m CONHA$, $(CH_2)_m CONA_2$, —O—$(CH_2)_n$-$Het^1$ or $Het^1$, Het denotes a monocyclic aromatic heterocycle having 1 to 3 N, O and/or S atoms, $Het^1$ denotes a monocyclic saturated heterocycle having 1 to 2 N and/or O atoms, which may be unsubstituted or monosubstituted by A or $(CH_2)_n OH$, Y denotes O, Z denotes —Ar, A denotes alkyl having 1 to 10 C atoms, in which, in addition, 1-7H atoms may be replaced by F and/or chlorine, Hal denotes F, Cl, Br or I, m denotes 0, 1 or 2, p denotes 1, 2, 3 or 4;

in Ii X denotes O,

Ar denotes Het which is unsubstituted or mono-, di- or trisubstituted by $R^1$, $R^1$ denotes $(CH_2)_m CONH_2$, $(CH_2)_m CONHA$ or $(CH_2)_m CONA_2$, Het denotes furyl, thienyl, pyrrolyl, imidazolyl, pyrazolyl, oxazolyl, thiazolyl, pyridyl, pyrimidinyl, pyridazinyl or pyrazinyl, $Het^1$ denotes a monocyclic saturated heterocycle having 1 to 2 N and/or O atoms, which may be unsubstituted or monosubstituted by A or $(CH_2)_n OH$, Y denotes O, Z denotes phenyl which is unsubstituted or mono-, di-, tri-, tetra- or pentasubstituted by A, OH, OA, $NH_2$, NHA, $NA_2$, —O—$(CH_2)_p$—$NH_2$, —O—$(CH_2)_p$—NHA, —O—$(CH_2)_p$—$NA_2$, —NH—$(CH_2)_p$—$NH_2$, —NH—$(CH_2)_p$—NHA, —NH—$(CH_2)_p$—$NA_2$, —NA-$(CH_2)_p$—$NH_2$, —NA-$(CH_2)_p$—NHA, —NA-$(CH_2)_p$—$NA_2$, —O—$(CH_2)_n$-$Het^1$, $Het^1$ or Hal, A denotes alkyl having 1 to 10 C atoms, in which, in addition, 1-7H atoms may be replaced by F and/or chlorine, Hal denotes F, Cl, Br or I, m denotes 0, 1 or 2, p denotes 1, 2, 3 or 4;

in Ij Ar denotes phenyl, naphthyl, biphenyl or Het, each of which is unsubstituted or mono-, di-, tri-, tetra- or pentasubstituted by $R^1$, X denotes —O— or —$(CH_2)_n$—, Y denotes O, Z denotes phenyl which is unsubstituted or mono-, di-, tri-, tetra- or pentasubstituted by $R^1$, -phenylene-X—Ar, —$CH_2$—Ar or —$CH_2$-phenylene-X—Ar, Het denotes a monocyclic aromatic heterocycle having 1 to 3 N, O and/or S atoms, $Het^1$ denotes a monocyclic saturated heterocycle having 1 to 2 N and/or O atoms, which may be unsubstituted or monosubstituted by A or $(CH_2)_n OH$, $R^1$ denotes A, OH, OA, $NH_2$, NHA, $NA_2$, Hal, $(CH_2)_m CONH_2$, $(CH_2)_m CONHA$, $(CH_2)_m CONA_2$, $S(O)_m A$, —O—$(CH_2)_p$—$NH_2$, —O—$(CH_2)_p$—NHA, —O—$(CH_2)_p$—$NA_2$, —NH—$(CH_2)_p$—$NH_2$, —NH—$(CH_2)_p$—NHA, —NH—$(CH_2)_p$—$NA_2$, —NA-$(CH_2)_p$—$NH_2$, —NA-$(CH_2)_p$—NHA, —NA-$(CH_2)_p$—$NA_2$, —O—$(CH_2)_n$—$Het^1$ or $Het^1$, A denotes alkyl having 1 to 10 C atoms, in which, in addition, 1-7H atoms may be replaced by F and/or chlorine, Hal denotes F, Cl, Br or I, n denotes 0, 1, 2 or 3, m denotes 0, 1 or 2, p denotes 1, 2, 3 or 4;

and pharmaceutically usable derivatives, salts, solvates, tautomers and stereoisomers thereof, including mixtures thereof in all ratios.

The compounds of the formula I and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use may also be made here of variants known per se which are not mentioned here in greater detail.

If desired, the starting materials can also be formed in situ by not isolating them from the reaction mixture, but instead immediately converting them further into the compounds of the formula I.

Compounds of the formula I can preferably be obtained by reacting compounds of the formula II with compounds of the formula Ill.

The compounds of the formula II are novel, those of the formula III are generally known.

In the compounds of the formula II, L preferably denotes Cl, Br, I or a free or reactively modified OH group, such as, for example, an activated ester, an imidazolide or alkylsulfonyloxy having 1-6 C atoms (preferably methylsulfonyloxy or trifluoromethylsulfonyloxy) or arylsulfonyloxy having 6-10 C atoms (preferably phenyl- or p-tolylsulfonyloxy).

Radicals of this type for activation of the carboxyl group in typical acylation reactions are described in the literature (for example in the standard works, such as Houben-Weyl, Methoden der organischen Chemie [Methods of Organic Chemistry], Georg-Thieme-Verlag, Stuttgart).

Activated esters are advantageously formed in situ, for example by addition of HOBt or N-hydroxysuccinimide.

Preference is given to the use of compounds of the formula II in which L denotes OH.

The reaction is generally carried out in an inert solvent, in the presence of an acid-binding agent, preferably an organic base, such as DIPEA, triethyl-amine, dimethylaniline, pyridine or quinoline, or an excess of the carboxyl component of the formula II.

The addition of an alkali or alkaline earth metal hydroxide, carbonate or bicarbonate or of another salt of a weak acid of the alkali or alkaline earth metals, preferably of potassium, sodium, calcium or caesium, may also be favourable.

Depending on the conditions used, the reaction time is between a few minutes and 14 days, the reaction temperature is between about 0° and 150°, normally between 15° and 90°, particularly preferably between 15 and 30° C.

Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, iso-propanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Pharmaceutical Salts and Other Forms

The said compounds according to the invention can be used in their final non-salt form. On the other hand, the present invention also relates to the use of these compounds in the form of their pharmaceutically acceptable salts, which can be derived from various organic and inorganic acids and bases by procedures known in the art. Pharmaceutically acceptable salt forms of the compounds of the formula I are for the most part prepared by conventional methods. If the compound of the formula I contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula I are likewise included. In the case of certain compounds of the formula I, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula I include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, di-gluconate, dihydrogenphosphate, dinitrobenzoate, dodecylsulfate, ethane-sulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese(III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula I which are derived from pharmaceutically acceptable organic non-toxic bases include salts of primary, secondary and tertiary amines, substituted amines, also including naturally occurring substituted amines, cyclic amines, and basic ion ex-changer resins, for example arginine, betaine, caffeine, chloroprocaine, choline, N,N'-dibenzylethylenediamine(benzathine), dicyclohexylamine, diethanolamine, diethylamine, 2-diethylaminoethanol, 2-dimethylamino-ethanol, ethanolamine, ethylenediamine, N-ethylmorpholine, N-ethyl-piperidine, glucamine, glucosamine, histidine, hydrabamine, isopropyl-amine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)methylamine (tromethamine), but this is not intended to represent a restriction.

Compounds of the present invention which contain basic nitrogen-containing groups can be quaternised using agents such as ($C_1$-$C_4$)alkyl halides, for example methyl, ethyl, isopropyl and tert-butyl chloride, bromide and iodide; di($C_1$-$C_4$) alkyl sulfates, for example dimethyl, diethyl and diamyl sulfate; ($C_{10}$-$C_{18}$)alkyl halides, for example decyl, dodecyl, lauryl, myristyl and stearyl chloride, bromide and iodide; and aryl(C$_1$-C$_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

The acid-addition salts of basic compounds of the formula I are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula I are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the term "pharmaceutically acceptable salt" in the present connection is taken to mean an active ingredient which comprises a compound of the formula I in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

The invention also relates to the intermediate compounds of the formula I-1

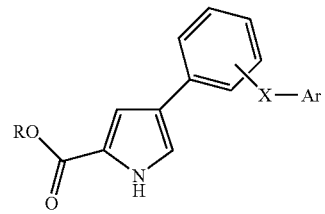

in which

Ar denotes phenyl, naphthyl, biphenyl or Het, each of which is un-substituted or mono-, di-, tri-, tetra- or pentasubstituted by R$^1$, X denotes —O—, —S—, —(CH$_2$)$_n$—, —C(=O)—, —CH(OH)—, —(CH$_2$)$_n$O—, —O(CH$_2$)$_n$—, —(CH$_2$)$_n$S—, —S(CH$_2$)$_n$—, —(CH$_2$)$_n$NH—, —NH(CH$_2$)$_n$—, —(CH$_2$)$_n$NA-, —NA(CH$_2$)$_n$—, —CHHal- or —C(Hal)$_2$-, R denotes H or A, Het denotes a mono- or bicyclic aromatic heterocycle having 1 to 4 N, O and/or S atoms, R$^1$ denotes A, Ar', OR$^3$, SR$^3$, OAr', SAr', N(R$^3$)$_2$, NHAr', Hal, NO$_2$, CN, (CH$_2$)$_m$COOR$^3$, (CH$_2$)$_m$CON(R$^3$)$_2$, COR$^3$, S(O)$_m$A, S(O)$_m$Ar', NHCOA, NHCOAr', NHSO$_2$A, NHSO$_2$Ar' or SO$_2$N(R$^3$)$_2$, R$^3$ denotes H, A or —(CH$_2$)$_n$Ar'—, Ar' denotes phenyl which is unsubstituted or mono-, di-, tri-, tetra- or pentasubstituted by A, Ph, OH, OA, SH, SA, OPh, SPh, NH$_2$, NHA, NA$_2$, NHPh, Hal, NO$_2$, CN, (CH$_2$)$_m$COOH, (CH$_2$)$_m$COOA, (CH$_2$)$_m$CONH$_2$, (CH$_2$)$_m$CONHA, CHO, COA, S(O)$_m$A, S(O)$_m$Ph, NHCOA, NHCOPh, NHSO$_2$A, NHSO$_2$Ph or SO$_2$NH$_2$, Ph denotes phenyl which is unsubstituted or mono-, di- or trisubstituted by A, Hal, CN, COOR, COOH, NH$_2$, NO$_2$, OH or OA, A denotes alkyl having 1 to 10 C atoms, in which, in addition, 1-7H atoms may be replaced by F and/or chlorine, Hal denotes F, Cl, Br or I, n denotes 0, 1, 2 or 3, m denotes 0, 1 or 2, and solvates, salts, tautomers and stereoisomers thereof, including mixtures thereof in all ratios.

Preference is given to compounds of the formula I-1 a in which the radicals not designated in greater detail have the meaning indicated for the formula I-1, but in which X denotes O, Ar denotes Het which is unsubstituted or mono-, di- or trisubstituted by R$^1$, R denotes H or A, R$^1$ denotes (CH$_2$)$_m$CONH$_2$, (CH$_2$)$_m$CONHA or (CH$_2$)$_m$CONA$_2$, Het denotes a monocyclic aromatic heterocycle having 1 to 3 N, O and/or S atoms, and salts, solvates, tautomers and stereoisomers thereof, including mixtures thereof in all ratios.

The invention furthermore relates to medicaments comprising at least one compound of the formula I and/or pharmaceutically usable derivatives, solvates and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be ad-ministered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be pre-pared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

The compounds of the formula I and salts, solvates and physiologically functional derivatives thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula I and the salts, solvates and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinyl-pyrrolidone, pyran copolymer, polyhydroxypropyl-methacrylamidophenol, polyhydroxyethylaspartamidophenol or polyethylene oxide polylysine, substituted by palmitoyl radicals. The compounds may furthermore be coupled to a class of biodegradable polymers which are suitable for achieving con-trolled release of a medicament, for example polylactic acid, poly-epsilon-caprolactone, polyhydroxybutyric acid, polyorthoesters, polyacetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be ad-ministered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multidose containers, for example sealed ampoules and vials, and stored in freeze-dried (lyophilised) state, so that only the addition of the sterile carrier liquid, for example water for injection purposes, immediately before use is necessary.

Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula I depends on a number of factors, including, for example, the age and weight of the animal, the precise condition which requires treatment, and its severity, the nature of the formulation and the method of administration, and is ultimately determined by the treating doctor or vet. However, an effective amount of a compound according to the invention for the treatment of neo-plastic growth, for example colon or breast carcinoma, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The invention furthermore relates to medicaments comprising at least one compound of the formula I and/or pharmaceutically usable derivatives, solvates and stereoisomers thereof, including mixtures thereof in all ratios, and at least one further medicament active ingredient.

The invention also relates to a set (kit) consisting of separate packs of (a) an effective amount of a compound of the formula I and/or pharmaceutically usable derivatives, solvates and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula I and/or pharmaceutically usable derivatives, solvates and stereoisomers thereof, including mixtures thereof in all ratios, and an effective amount of a further medicament active ingredient in dissolved or lyophilised form.

Use

As explained, the signalling pathways are relevant for various disorders. Accordingly, by interacting with one or more of said signalling pathways, the pyrrole derivatives are useful in the prevention and/or the treatment of disorders that are dependent on said signalling pathways.

The compounds according to the invention are preferably kinase modulators and more preferably kinase inhibitors. According to the invention, kinases include, but are not limited to, one or more Raf kinases, one or more Tie kinases, one or more VEGFR kinases, one or more PDGFR kinases, p38 kinase and/or SAPK2alpha.

The invention relates to the use of compounds of the formula I, and pharmaceutically usable derivatives, solvates and stereoisomers thereof, including mixtures thereof in all ratios, for the preparation of a medicament for the treatment of diseases in which the inhibition, regulation and/or modulation of kinase signal transduction plays a role.

Preference is given here to Raf kinases.

The compounds of the formula I are suitable for the preparation of a medicament for the treatment of diseases which are caused, mediated and/or propagated by Raf kinases, where the Raf kinase is selected from the group consisting of A-Raf, B-Raf and Raf-1.

Preference is given to the use for the treatment of diseases, preferably from the group hyperproliferative and non-hyperproliferative diseases.

These are cancerous diseases or non-cancerous diseases.

The non-cancerous diseases are selected from the group consisting of psoriasis, arthritis, inflammation, endometriosis, scarring, benign prostatic hyperplasia, immunological diseases, autoimmune diseases and immuno-deficiency diseases.

The cancerous diseases are selected from the group consisting of dermatological tumours, haematological tumours, sarcomas, squamous epithelium cancer, stomach cancer, head cancer, neck cancer, oesophageal cancer, lymphoma, ovarian cancer, cervical cancer and/or prostate cancer. Modulation of the Raf kinase pathway plays a even more important role in various cancer types which show a constitutive activation of the Raf kinase-dependent signalling pathway, such as melanoma, colorectal cancer, lung cancer, brain cancer, pancreatic cancer, breast cancer, gynaecological cancer, ovarian cancer, thyroid cancer, chronic leukaemia and acute leukaemia, bladder cancer, hepatic cancer and/or renal cancer. Modulation of the Raf kinase pathway also plays an important role in infection diseases, preferably the infection diseases as mentioned above/below and especially in *Helicobacter pylori* infections, such as *Helicobacter pylori* infection during peptic ulcer disease.

One or more of the signalling pathways mentioned above/below and especially the VEGFR kinase pathway, plays an important role in angiogenesis. Accordingly, due to the kinase modulating or inhibiting properties of the compounds according to the invention, the compounds according to the invention are suitable for the prophylaxis and/or treatment of pathological processes or disorders caused, mediated and/or propagated by angiogenesis, for example by inducing anti-angiogenesis. Pathological processes or disorders caused, mediated and/or propagated by angiogenesis include, but are not limited to, tumours, especially solid tumours, arthritis, especially rheumatic or rheumatoid arthritis, diabetic retinopathy, psoriasis, restenosis; fibrotic disorders; mesangial cell proliferative disorders, diabetic nephropathy, malignant nephrosclerosis, thrombotic microangiopathy syndromes, organ transplant rejection, glomerulopathies, metabolic disorders, inflammation and neurodegenerative diseases, and especially solid tumours, rheumatic arthritis, diabetic retinopathy and psoriasis.

Modulation of the p38 signalling pathway plays an important role in various cancerous and also in various non-cancerous disorders, such as fibrosis, atherosclerosis, restenosis, vascular disease, cardiovascular disease, inflammation, renal disease and/or angiogenesis, and especially non-cancerous disorders, such as rheumatoid arthritis, inflammation, autoimmune disease, chronic obstructive pulmonary disease, asthma and/or inflammatory bowel disease.

Modulation of the PDGF signalling pathway plays an important role in various cancerous and also in various non-cancerous disorders, such as rheumatoid arthritis, inflammation, autoimmune disease, chronic obstructive pulmonary disease, asthma and/or inflammatory bowel disease, and especially non-cancerous disorders, such as fibrosis, atherosclerosis, restenosis, vascular disease, cardiovascular disease, inflammation, renal disease and/or angiogenesis.

The present compounds are also suitable for combination with known anti-cancer agents. These known anti-cancer agents include the following: oestrogen receptor modulators, androgen receptor modulators, retinoid receptor modulators, cytotoxic agents, antiproliferative agents, prenyl-protein transferase inhibitors, HMG-CoA reductase inhibitors, HIV protease inhibitors, reverse transcriptase inhibitors and other angiogenesis inhibitors. The present compounds are particularly suitable for administration at the same time as radiotherapy.

"Oestrogen receptor modulators" refers to compounds which interfere with or inhibit the binding of oestrogen to the receptor, regardless of mechanism. Examples of oestrogen receptor modulators include, but are not limited to, tamoxifen, raloxifene, idoxifene, LY353381, LY 117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]phenyl 2,2-dimethyl-propanoate, 4,4'-dihydroxybenzophenone-2,4-dinitrophenylhydrazone and SH646.

"Androgen receptor modulators" refers to compounds which interfere with or inhibit the binding of androgens to the receptor, regardless of mechanism. Examples of androgen receptor modulators include finasteride and other 5α-reductase inhibitors, nilutamide, flutamide, bicalutamide, liarozole and abiraterone acetate.

"Retinoid receptor modulators" refers to compounds which interfere with or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl)retinamide and N-4-carboxyphenyl-retinamide.

"Cytotoxic agents" refers to compounds which result in cell death primarily through direct action on the cellular function or inhibit or interfere with cell myosis, including alkylating agents, tumour necrosis factors, intercalators, microtubulin inhibitors and topoisomerase inhibitors.

Examples of cytotoxic agents include, but are not limited to, tirapazimine, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosylate, trofosfamide, nimustine, dibrospidium chloride, pumitepa, lobaplatin, satraplatin, profiromycin, cisplatin, irofulven, dexifosfamide, cis-aminedichloro(2-methylpyridine)platinum, benzylguanine, glufosfamide, GPX100, (trans,trans,trans)bis-mu-(hexane-1,6-diamine)mu-[diamine-platinum(II)]bis[diamine(chloro)platinum(II)]tetrachloride, diarizidinyl-spermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755 and 4-demethoxy-3-deamino-3-aziridinyl-4-methylsulfonyldaunorubicin (see WO 00/50032).

Examples of microtubulin inhibitors include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl)benzenesulfonamide, anhydrovinblastine, N,N-dimethyl-L-valyl-L-valyl-N-methyl-L-valyl-L-prolyl-L-proline-t-butylamide, TDX258 and BMS188797.

Some examples of topoisomerase inhibitors are topotecan, hycaptamine, irinotecan, rubitecan, 6-ethoxypropionyl-3',4'-O-exobenzylidenechartreusin, 9-methoxy-N,N-dimethyl-5-nitropyrazolo[3,4,5-kl]acridine-2-(6H)propanamine, 1-amino-9-ethyl-5-fluoro-2,3-dihydro-9-hydroxy-4-methyl-1H, 12H-benzo[de]pyrano[3',4':b,7]indolizino[1,2b]quinoline-10,13(9H,15H)dione, lurtotecan, 7-[2-(N-isopropylamino)ethyl]-(20S)-camptothecin, BNP1350, BNPI1100, BN80915, BN80942, etoposide phosphate, teniposide, sobuzoxane, 2'-dimethylamino-2'-deoxyetoposide, GL331, N-[2-(dimethylamino)ethyl]-9-hydroxy-5,6-dimethyl-6H-pyrido[4,3-b]carbazole-1-carboxamide, asulacrine, (5a,5aB,8aa, 9b)-9-[2-[N-[2-(di-methylamino)ethyl]-N-methylamino]

ethyl]-5-[4-hydroxy-3,5-dimethoxy-phenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-th ioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c]quinolin-7-one and dimesna.

"Antiproliferative agents" include antisense RNA and DNA oligonucleotides such as G3139, ODN698, RVASK-RAS, GEM231 and INX3001 and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, neizarabine, 2'-deoxy-2'-methylidenecytidine, 2'-fluoromethylene-2'-deoxycytidine, N-[5-(2,3-di-hydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-mannohepto-pyranosyl]adenine, aplidine, ecteinascidin, troxacitabine, 4-[2-amino-4-oxo-4,6,7,8-tetrahydro-3H-pyrimidino[5,4-b]-1,4-thiazin-6-yl-(S)-ethyl]-2,5-thienoyl-L-glutamic acid, aminopterin, 5-fluorouracil, alanosine, 11-acetyl-8-(carbamoyloxymethyl)-4-formyl-6-methoxy-14-oxa-1,11-diazatetracyclo-(7.4.1.0.0)tetradeca-2,4,6-trien-9-ylacetic acid ester, swainsonine, lometrexol, dexrazoxane, methioninase, 2'-cyano-2'-deoxy-N-4-palmitoyl-1-B-D-arabinofuranosyl cytosine and 3-aminopyridine-2-carboxaldehyde thio-semicarbazone. "Antiproliferative agents" also include monoclonal anti-bodies to growth factors other than those listed under "angiogenesis inhibitors", such as trastuzumab, and tumour suppressor genes, such as p53, which can be delivered via recombinant virus-mediated gene transfer (see U.S. Pat. No. 6,069,134, for example).

Assays

The assays are known from the literature and can readily be performed by the person skilled in the art (see, for example, Dhanabal et al., *Cancer Res.* 59:189-197; Xin et al., *J. Biol. Chem.* 274:9116-9121; Sheu et al., *Anticancer Res.* 18:4435-4441; Ausprunk et al., *Dev. Biol.* 38:237-248; Gimbrone et al., *J. Natl. Cancer Inst.* 52:413-427; Nicosia et al., *In Vitro* 18:538-549).

In general, compounds according to the invention are to be regarded as suitable kinase-modulators and especially suitable kinase inhibitors according to the invention if they show an effect or an activity to one or more kinases, preferably to one or more Raf kinases, which is preferably, determined as $IC_{50}$ value, in the region of 100 µmol or below, preferably 10 µmol or below, more preferably in the region of 3 µmol or below, even more preferably in the region of 1 µmol or below and most preferably in the nanomolar range. Especially preferred for use according to the invention are kinase inhibitors as defined above/below which show an activity, deter-mined as $IC_{50}$ value, to one or more Raf kinases, preferably comprising A-Raf, B-Raf and c-Raf1 or consisting of A-Raf, B-Raf and c-Raf1 and more preferably comprising c-Raf1 or consisting of c-Raf1, in the region of 0.5 mmol or below and especially in the region of 0.1 µmol or below. In many cases, an $IC_{50}$ value at the lower end of the given ranges is advantageous and in some cases it is highly desirable that the $IC_{50}$ value is as small as possible or the $IC_{50}$ values are as small as possible, but in general $IC_{50}$ values which are between the above given upper limits and a lower limit in the region of 0.0001 µmol, 0.001 µmol, 0.01 µmol or even above 0.1 µmol are sufficient to indicate the desired pharmaceutical activity. However, the activities measured can vary depending on the respective testing system or assay chosen.

Alternatively, the advantageous biological activity of the compounds according to the invention can easily be demonstrated in in vitro assays, such as in vitro proliferation assays or in vitro growth assays. Suitable in vitro assays are known in the art, for example from the literature cited herein and the references cited in the literature, or can be performed as described below, or can be developed and/or performed in an analogous manner thereto.

As an example for an in vitro growth assay, human tumour cell lines, for example HCT116, DLD-1 or MiaPaCa, containing mutated K-Ras genes can be used in standard proliferation assays, for example for anchorage-dependent growth on plastic or anchorage-independent growth in soft agar. Human tumour cell lines are commercially available, for example from ATCC (Rockville Md.), and can be cultured by methods known in the art, for example in RPMI with 10% of heat-deactivated foetal bovine serum and 200 mM glutamine. Cell culture media, foetal bovine serum and additives are commercially available, for example from Invitrogen/Gibco/BRL (Karlsruhe, Germany) and/or QRH Biosciences (Lenexa, Kans.). In a standard proliferation assay for anchorage-dependent growth, $3\times10^3$ cells can be seeded into 96-well tissue culture plates and allowed to attach, for example overnight at 37° C. in a 5% $CO_2$ incubator. Compounds can be titrated in media in dilution series and added to 96-well cell cultures. Cells are allowed to grow, for example for 1 to 5 days, typically with feeding of fresh compound containing media at about half of the time of the growing period, for example on day 3 if the cells are allowed to grow for 5 days. Proliferation can be monitored by methods known in the art, such as measurement of metabolic activity, for example with standard XTT colorimetric assay (Boehringer Mannheim) measured by standard ELISA plate reader at OD 490/560, by measuring $^3$H-thymidine incorporation into DNA following an 8 h culture with 1 pCu 3H-thymidine, harvesting the cells onto glass fibre mats using a cell harvester and measuring $^3$H-thymidine incorporation by liquid scintillation counting, or by staining techniques, such as Crystal Violet staining. Other suitable cellular assay systems are known in the art.

Alternatively, for anchorage-independent cell growth, cells can be plated at $1\times10^3$ to $3\times10^3$ in 0.4% of Seaplaque agarose in RPMI complete media, overlaying a bottom layer containing only 0.64% agar in RPMI complete media, for example in 24-well tissue culture plates. Complete media plus dilution series of compounds can be added to wells and incubated, for example at 37° C. in a 5% $CO_2$ incubator for a sufficient time, for example 10-14 days, preferably with repeated feedings of fresh media containing compound, typically at 3-4 day intervals. Colony formation and total cell mass can be monitored, average colony size and number of colonies can be quantified by methods known in the art, for example using image capture technology and image analysis software. Image capture technology and image analysis software, such as Image Pro Plus or media Cybernetics.

Above and below, all temperatures are indicated in ° C. In the following examples, "conventional work-up" means: water is added if necessary, the pH is adjusted, if necessary, to a value of between 2 and 10, depending on the constitution of the end product, the mixture is extracted with ethyl acetate or dichloromethane, the phases are separated, the organic phase is dried over sodium sulfate and evaporated, and the product is purified by chromatography on silica gel and/or by crystallisation. Rf values on silica gel; eluent: ethyl acetate/methanol 9:1.

Mass spectrometry (MS): EI (electron impact ionisation) M+FAB (fast atom bombardment) (M+H)+ESI (electrospray ionisation) (M+H)+

APCI-MS (atmospheric pressure chemical ionisation–mass spectrometry) (M+H)+.

EXAMPLE 1

Preparation of N-methyl-4-{4-[5-(4-chloro-3-trifluoromethylmethylphenylcarbamoyl)-1H-pyrrol-3-yl]phenoxy}pyridine-2-carboxamide (6)

1.1 Synthesis of [2-(4-benzyloxyphenyl)-3-dimethylaminoallylidene]di-methylammonium perchlorate (1)

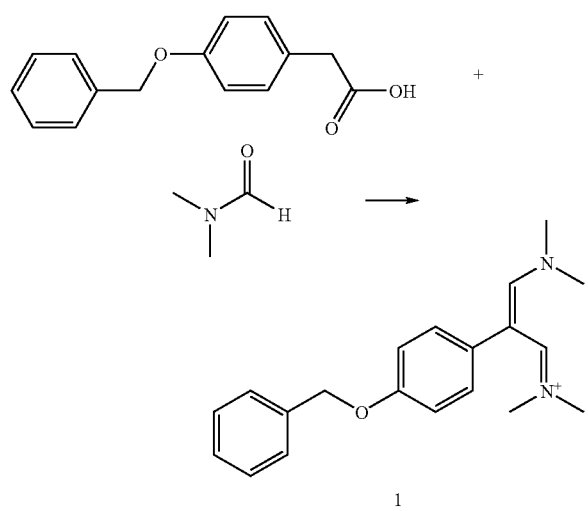

6 g of (4-benzyloxyphenyl)acetic acid are added under a protective-gas atmosphere to a mixture of 6.7 ml of phosphoryl chloride (73.1 mmol) in 30 ml of dimethylformamide, and the mixture is stirred at 70° C. for 4 hours. After cooling, the solvent is stripped off, ice-water is added to the residue, and 3.4 g of sodium perchlorate (24.4 mmol) dissolved in 20 ml of water are added. The precipitated solid is filtered off and washed with water. Yield: 9.9 g (98%) of 1, yellow crystals.

1.2 Synthesis of ethyl 4-(4-benzyloxyphenyl)-1H-pyrrole-2-carboxylate (2)

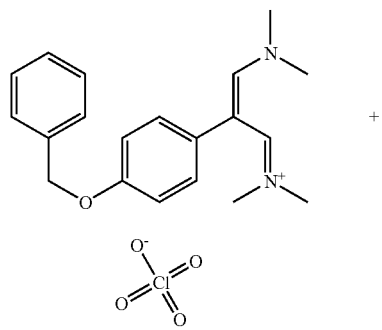

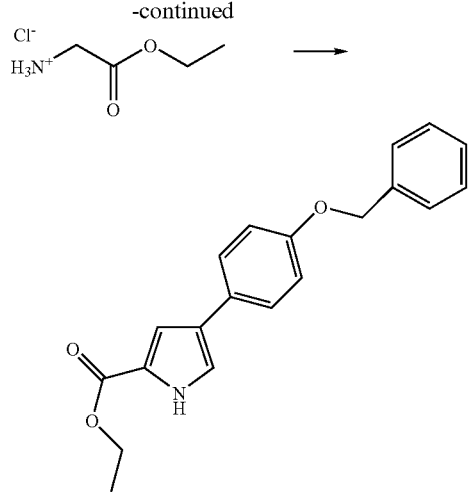

4.5 g of [2-(4-benzyloxyphenyl)-3-dimethylaminoallylidene]dimethylammonium perchlorate 1 are added under a protective-gas atmosphere to a mixture of 10 ml of a 20% sodium ethoxide solution in ethanol (27.4 mmol) and 2.3 g (16.4 mmol) of glycine ethyl ester hydrochloride in 130 ml of ethanol, and the mixture is heated under reflux for 24 hours. After cooling, the solvent is stripped off, the residue is taken up in water, and the product is extracted with ethyl acetate. The combined organic phases are dried over sodium sulfate. The product is obtained after filtration and removal of the solvent by distillation.

Yield: 3.4 g (91%) of 2, brown crystals.

1.3 Synthesis of ethyl 4-(4-hydroxyphenyl)-1H-pyrrole-2-carboxylate (3)

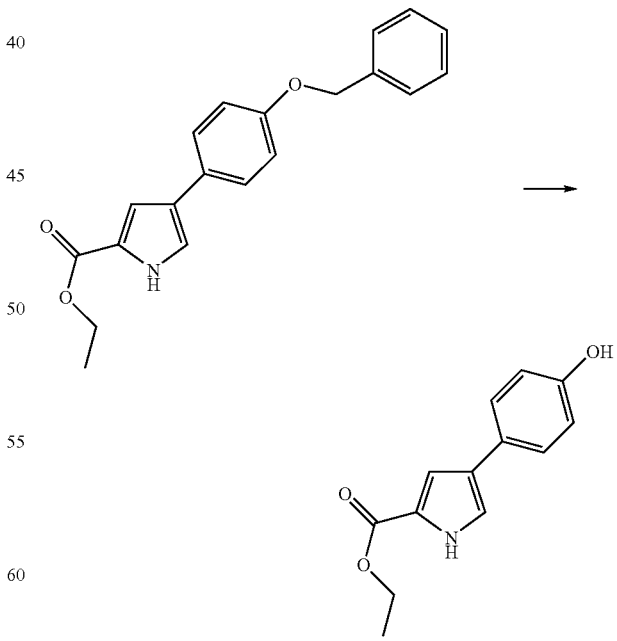

1 g of catalyst (5% palladium on activated carbon) is added to 4.5 g (13.3 mmol) of ethyl 4-(4-benzyloxyphenyl)-1H- pyrrole-2-carboxylate 2 in 90 ml of ethyl acetate, and the mixture is hydrogenated using 0.3 l of $H_2$. The solvent is stripped off, and the product is dried at 50 C under reduced pressure for 1 hour.

Yield: 2.8 g (91%) of 3, white crystals.

1.4 Synthesis of ethyl 4-[4-(2-methylcarbamoylpyridin-4-yloxy)phenyl]-1H-pyrrole-2-carboxylate (4)

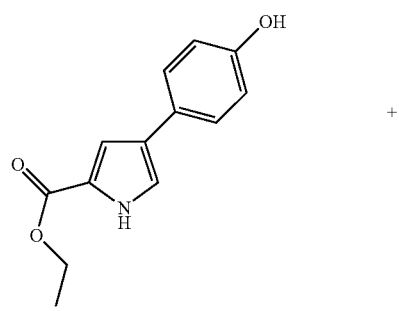

+

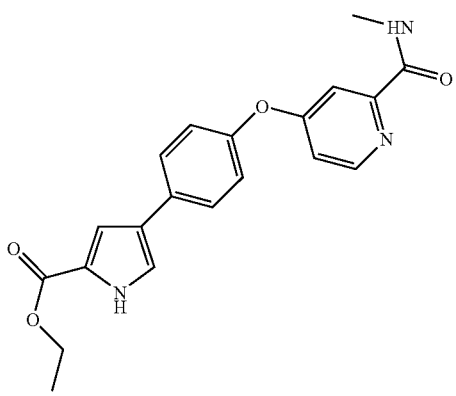

1.0 g (4.3 mmol) of ethyl 4-(4-hydroxyphenyl)-1H-pyrrole-2-carboxylate 3 and 1.1 g (6.5 mmol) of N-methyl-4-chloropyridine-2-carboxamide A are mixed thoroughly and slowly heated to 160° C. After 48 hours at 160° C., the reaction mixture is cooled to just above the solidification point, ethyl acetate is added, and the mixture is washed twice with 2N sodium hydroxide solution and water. After the organic phase has been dried and the solvent has been removed by distillation, the crude product is obtained as a brown oil. This is purified by normal-phase column chromatography (eluent petroleum ether/ethyl acetate).

Yield: 0.7 g (40%) of 4 yellowish crystals.

1.5 Synthesis of 4-[4-(2-methylcarbamoylpyridin-4-yloxy)phenyl]-1H-pyrrole-2-carboxylic acid (5)

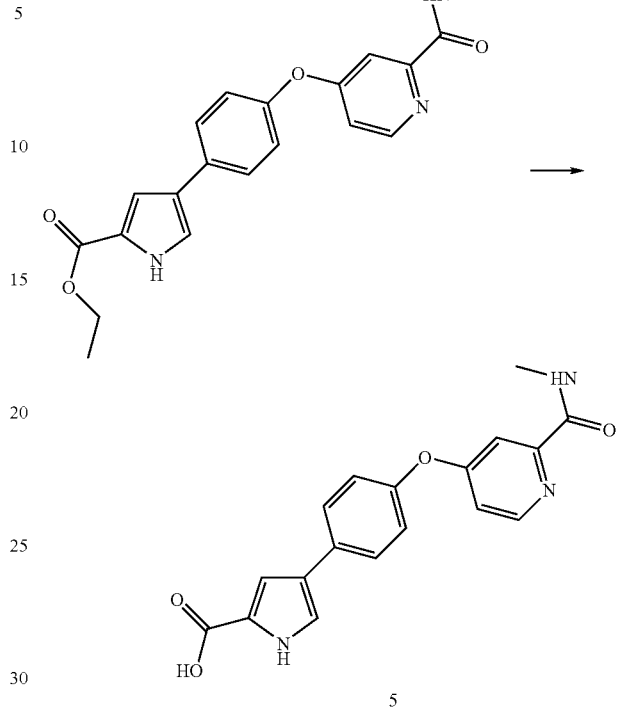

0.6 g (1.56 mmol) of ethyl 4-[4-(2-methylcarbamoylpyridin-4-yloxy)phenyl]-1H-pyrrole-2-carboxylate 4 are stirred at 60° C. for 16 hours in 5 ml of 2 N sodium hydroxide solution and 20 ml of ethanol. After the ethanol has been removed by distillation, the mixture is neutralised using concentrated hydrochloric acid and extracted with ethyl acetate, and the combined organic phases are dried over sodium sulfate. After filtration and evaporation, the product is crystallised from methanol.

Yield: 0.46 g (85%) of 5 yellow crystals.

1.6 Synthesis of N-methyl-4-{4-[5-(4-chloro-3-trifluoromethylphenylcarbamoyl)-1H-pyrrol-3-yl]phenoxy}pyridine-2-carboxamide (6)

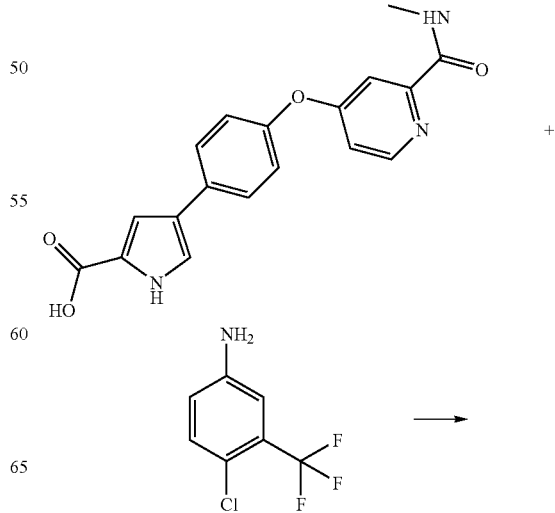

+

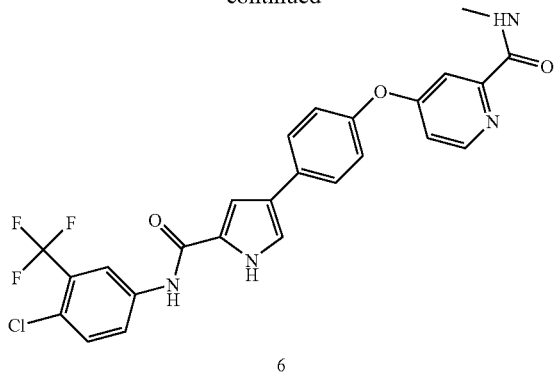

6

100 mg (0.3 mmol) of 4-[4-(2-methylcarbamoylpyridin-4-yloxy)phenyl]-1H-pyrrole-2-carboxylic acid 5 are dissolved in 3 ml of dimethylformamide, and 61 mg (0.3 mmol) of 5-amino-2-chlorobenzotrifluoride, 57 mg (0.3 mmol) of N(-3-dimethylaminopropyl)-N'-ethylcarbodiimide hydrochloride and 45.3 mg (0.3 mmol) of 1-hydroxybenzotriazole hydrate are added. The mixture is stirred at room temperature for 48 hours. Water is added to the reaction mixture, and the product is extracted with ethyl acetate. The combined organic phases are dried over sodium sulfate. The crude product is purified by normal-phase column chromatography (eluent petroleum ether/ethyl acetate).

Yield: 25 mg (17%) of 6 yellow crystals HPLC retention time tr [min]: 3.64Conditions: gradient 3.5 min Flow rate: 1.5 ml/min from 80:20 to 0:100 [H$_2$O/acetonitrile]H$_2$O or acetonitrile contains 0.01% of TFA Column: Chromolith Speed-ROD RP 18 e 50-4.6

The following compounds are obtained analogously
N-methyl-4-{3-[5-(4-chloro-3-trifluoromethylmethylphenylcarbamoyl)-1H-pyrrol-3-yl]phenoxy}pyridine-2-carboxamide, tr 3.65; EI m/e 515;
N-methyl-4-{4-[5-(3-chloro-4-methylphenylcarbamoyl)-1H-pyrrol-3-yl]-phenoxy}pyridine-2-carboxamide, tr 3.48;
N-methyl-4-{4-[5-(2-methoxy-5-trifluoromethylphenylcarbamoyl)-1H-pyrrol-3-yl]phenoxy}pyridine-2-carboxamide, tr 3.54;
N-methyl-4-{3-[5-(3-chloro-4-methylmethylphenylcarbamoyl)-1H-pyrrol-3-yl]phenoxy}pyridine-2-carboxamide, tr 3.49; EI m/e 461;
N-methyl-4-{4-[5-(3-chloro-6-methoxymethylphenylcarbamoyl)-1H-pyrrol-3-yl]phenoxy}pyridine-2-carboxamide, tr 3.46;
N-methyl-4-{3-[5-(3-chloro-6-methoxymethylphenylcarbamoyl)-1H-pyrrol-3-yl]phenoxy}pyridine-2-carboxamide, tr 3.47; EI m/e 477;
N-methyl-4-{3-[5-(2-methoxy-5-trifluoromethylmethylphenyl-carbamoyl)-1H-pyrrol-3-yl]phenoxy}pyridine-2-carboxamide, tr 3.55; EI m/e 510;
N-methyl-4-{3-[5-(2,5-dimethoxy-4-chlorophenylcarbamoyl)-1H-pyrrol-3-yl]phenoxy}pyridine-2-carboxamide, tr 3.46; EI m/e 507;
N-methyl-4-{3-[5-(4-bromo-3-trifluoromethylphenylcarbamoyl)-1H-pyrrol-3-yl]phenoxy}pyridine-2-carboxamide, tr 3.70; EI m/e 559;
N-methyl-4-{3-[5-(3-trifluoromethoxyphenylcarbamoyl)-1H-pyrrol-3-yl]-phenoxy}pyridine-2-carboxamide, tr 3.50; EI m/e 480;
N-methyl-4-{3-[5-(4-tert-butylphenylcarbamoyl)-1H-pyrrol-3-yl]-phenoxy}pyridine-2-carboxamide, tr 3.67; EI m/e 469;
N-methyl-4-{3-[5-(3,4-dichlorophenylcarbamoyl)-1H-pyrrol-3-yl]-phenoxy}pyridine-2-carboxamide, tr 3.63; EI m/e 481;
N-methyl-4-{3-[5-(4-chloro-3-methyl-6-methoxyphenylcarbamoyl)-1H-pyrrol-3-yl]phenoxy}pyridine-2-carboxamide, tr 3.63; EI m/e 491;
N-methyl-4-{3-[5-(2,4-dimethoxy-5-trifluoromethoxyphenylcarbamoyl)-1H-pyrrol-3-yl]phenoxy}pyridine-2-carboxamide, tr 3.69; EI m/e 540;
N-methyl-4-{3-[5-(2-dimethylamino-5-trifluoromethylphenylcarbamoyl)-1H-pyrrol-3-yl]phenoxy}pyridine-2-carboxamide, tr 3.77; EI m/e 524;
N-methyl-4-{3-[5-(2-(2-methylaminoethoxy)-5-methylphenylcarbamoyl)-1H-pyrrol-3-yl]phenoxy}pyridine-2-carboxamide, tr 2.65; EI m/e 500;
N-methyl-4-{3-[5-(2-(2-dimethylaminoethoxy)-5-methylphenylcarbamoyl)-1H-pyrrol-3-yl]phenoxy}pyridine-2-carboxamide, tr 2.45; EI m/e 514;
N-methyl-4-{3-[5-(2-[(2-dimethylaminoethyl)methylamino]-5-methyl-phenylcarbamoyl)-1H-pyrrol-3-yl]phenoxy}pyridine-2-carboxamide, tr 2.34; EI m/e 527.

EXAMPLE 2

The following compounds are obtained analogously to Example 1
N-[4-(pyridin-4-yloxy)phenyl]-4-(3-trifluoromethylphenyl)-1H-pyrrole-2-carboxamide

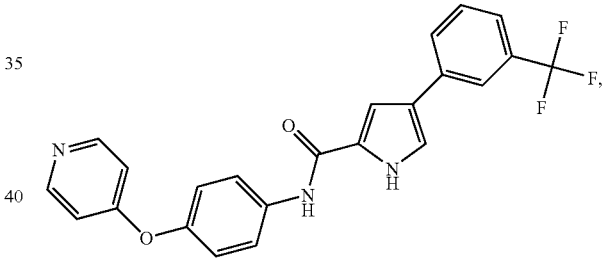

N-methyl-4-[4-({1-[4-(3-trifluoromethylphenyl)-1H-pyrrol-2-yl]-methanoyl}amino)phenoxy]pyridine-2-carboxamide

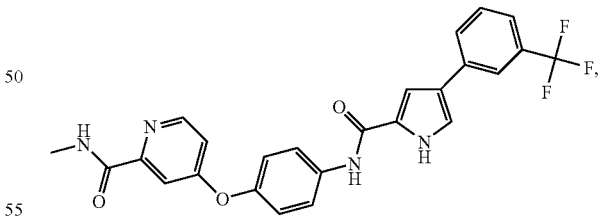

N-[4-(pyridin-3-yloxy)phenyl]-4-(3-trifluoromethylphenyl)-1H-pyrrole-2-carboxamide,
N-[4-(pyridin-4-yloxy)phenyl]-4-(4-phenoxyphenyl)-1H-pyrrole-2-carboxamide,
N-methyl-4-[4-({1-[4-(4-chlorophenyl)-1H-pyrrol-2-yl]methanoyl}-amino)phenoxy]pyridine-2-carboxamide,
N-[4-(pyridin-3-yloxy)phenyl]-4-(4-chlorophenyl)-1H-pyrrole-2-carboxamide,
N-(3-trifluoromethylphenyl)-4-(4-phenoxyphenyl)-1H-pyrrole-2-carboxamide, N-(4-chlorophenyl)-4-(4-phenoxyphenyl)-1H-pyrrole-2-carboxamide,
N-[4-(pyridin-3-yloxy)phenyl]-4-(4-methylsulfonylphenyl)-1H-pyrrole-2-carboxamide,
35 N-methyl-4-{4-[({1-[4-(4-methylsulfonylphenyl)-1H-pyrrol-2-yl]methanoyl}amino)methyl]phenoxy}pyridine-2-carboxamide,
N-3-(pyridin-4-yloxy)benzyl-4-(4-methylsulfonylphenyl)-1H-pyrrole-2-carboxamide.

The following examples relate to medicaments:

EXAMPLE A

Injection Vials

A solution of 100 g of an active ingredient of the formula I and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

EXAMPLE B

Suppositories

A mixture of 20 g of an active ingredient of the formula I with 100 g of soya lecithin and 1400 g of cocoa butter is melted, poured into moulds and al-lowed to cool. Each suppository contains 20 mg of active ingredient.

EXAMPLE C

Solution

A solution is prepared from 1 g of an active ingredient of the formula I, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

EXAMPLE D

Ointment 500 mg of an active ingredient of the formula I are mixed with 99.5 g of Vaseline under aseptic conditions.

EXAMPLE E

Tablets

A mixture of 1 kg of active ingredient of the formula I, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

EXAMPLE F

Dragees

Tablets are pressed analogously to Example E and subsequently coated in a conventional manner with a coating of sucrose, potato starch, talc, tragacanth and dye.

EXAMPLE G

Capsules 2 kg of active ingredient of the formula I are introduced into hard gelatine capsules in a conventional manner in such a way that each capsule contains 20 mg of the active ingredient.

EXAMPLE H

Ampoules

A solution of 1 kg of active ingredient of the formula I in 60 l of bidistilled water is sterile filtered, transferred into ampoules, lyophilised under sterile conditions and sealed under sterile conditions. Each ampoule contains 10 mg of active ingredient.

The invention claimed is:
1. A compound selected from:
N-methyl-4-{4-[5-(4-chloro-3-trifluoromethylphenylcarbamoyl)-1H-pyrrol-3-yl]-phenoxy}pyridine-2-carboxamide,
N-methyl-4-{3-[5-(4-chloro-3-trifluoromethylphenylcarbamoyl)-1H-pyrrol-3-yl]-phenoxy}pyridine-2-carboxamide,
N-methyl-4-{4-[5-(3-chloro-4-methylphenylcarbamoyl)-1H-pyrrol-3-yl]phenoxy}-pyridine-2-carboxamide,
N-methyl-4-{4-[5-(2-methoxy-5-trifluoromethylphenylcarbamoyl)-1H-pyrrol-3-yl]-phenoxy}pyridine-2-carboxamide,
N-methyl-4-{3-[5-(3-chloro-4-methylphenylcarbamoyl)-1H-pyrrol-3-yl]phenoxy}-pyridine-2-carboxamide,
N-methyl-4-{4-[5-(3-chloro-6-methoxyphenylcarbamoyl)-1H-pyrrol-3-yl]phenoxy}-pyridine-2-carboxamide,
N-methyl-4-{3-[5-(3-chloro-6-methoxyphenylcarbamoyl)-1H-pyrrol-3-yl]phenoxy}-pyridine-2-carboxamide,
N-methyl-4-{3-[5-(2-methoxy-5-trifluoromethylphenylcarbamoyl)-1H-pyrrol-3-yl]-phenoxy}pyridine-2-carboxamide,
N-methyl-4-{3-[5-(2,5-dimethoxy-4-chlorophenylcarbamoyl)-1H-pyrrol-3-yl]-phenoxy}pyridine-2-carboxamide,
N-methyl-4-{3-[5-(4-bromo-3-trifluoromethylphenylcarbamoyl)-1H-pyrrol-3-yl]-phenoxy}pyridine-2-carboxamide,
N-methyl-4-{3-[5-(3-trifluoromethoxyphenylcarbamoyl)-1H-pyrrol-3-yl]phenoxy}-pyridine-2-carboxamide,
N-methyl-4-{3-[5-(4-tert-butylphenylcarbamoyl)-1H-pyrrol-3-yl]phenoxy}pyridine-2-carboxamide,
N-methyl-4-{3-[5-(3,4-dichlorophenylcarbamoyl)-1H-pyrrol-3-yl]phenoxy}pyridine-2-carboxamide,
N-methyl-4-{3-[5-(4-chloro-3-methyl-6-methoxyphenylcarbamoyl)-1H-pyrrol-3-yl]-phenoxy}pyridine-2-carboxamide,
N-methyl-4-{3-[5-(2,4-dimethoxy-5-trifluoromethoxyphenylcarbamoyl)-1H-pyrrol-3-yl]phenoxy}pyridine-2-carboxamide,
N-methyl-4-{3-[5-(2-dimethylamino-5-trifluoromethylphenylcarbamoyl)-1H-pyrrol-3-yl]phenoxy}pyridine-2-carboxamide,
N-methyl-4-{3-[5-(2-(2-methylaminoethoxy)-5-methylphenylcarbamoyl)-1H-pyrrol-3-yl]phenoxy}pyridine-2-carboxamide,

N-methyl-4-{3-[5-(2-(2-dimethylaminoethoxy)-5-methylphenylcarbamoyl)-1H-pyrrol-3-yl]phenoxy}pyridine-2-carboxamide,
N-methyl-4-{3-[5-(2-[(2-dimethylaminoethyl)methylamino]-5-methyl-phenylcarbamoyl)-1H-pyrrol-3-yl]phenoxy}pyridine-2-carboxamide,
and pharmaceutically acceptable salts and stereoisomers thereof, including mixtures thereof in all ratios.

2. A process for the preparation of a compound according to 1, said process comprising:
reacting a compound of formula II

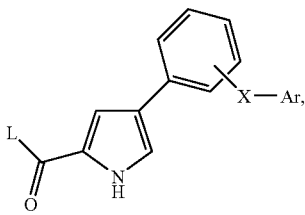

wherein L is Cl, Br, I or a free or reactively functionally modified OH group, X is O, and Ar is pyridinyl,
with a compound of formula III

Z-NH$_2$    III wherein Z is 4-chloro-3-trifluoromethylphenyl, 3-chloro-4-methylphenyl, 2-methoxy-5-trifluoromethylphenyl, 3-chloro-6-methoxyphenyl, 2,5-dimethoxy-4-chlorophenyl, 4-bromo-3-trifluoromethylphenyl, 3-trifluoromethoxyphenyl, 4-tert-butylphenyl, 3,4-dichlorophenyl, 4-chloro-3-methyl-6-methoxyphenyl, 2,4-dimethoxy-5-trifluoromethoxyphenyl, 2-dimethylamino-5-trifluoromethylphenyl, 2-dimethylamino-5-trifluoromethylphenyl, 2-(2-methylaminoethoxy)-5-methylphenyl, 2-(2-dimethylaminoethoxy)-5-methyl, or 2-[(2-dimethylaminoethyl)methylamino]-5-methylphenyl,
and, if the resultant compound is a base or acid, optionally converting said base or acid into a pharmaceutically acceptable salt thereof.

3. A pharmaceutical composition comprising at least one compound according to claim 1 and at least one excipient and/or adjuvant.

4. A compound of formula I-1

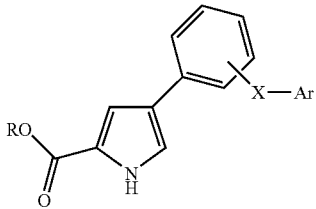

wherein
Ar is pyridinyl which is unsubstituted or mono-, di-, tri-, tetra- or pentasubstituted by R$^1$,
X is —O—,
R is H or A,
R$^1$ is A, Ar', OR$^3$, SR$^3$, OAr', SAr', N(R$^3$)$_2$, NHAr', Hal, NO$_2$, CN, (CH$_2$)$_m$COOR$^3$, (CH$_2$)$_m$CON(R$^3$)$_2$, COR$^3$, S(O)$_m$A, S(O)$_m$Ar', NHCOA, NHCOAr', NHSO$_2$A, NHSO$_2$Ar', or SO$_2$N(R$^3$)$_2$,
R$^3$ is H, A or —(CH$_2$)$_n$AR'—,
Ar' is phenyl which is unsubstituted or mono-, di-, tri-, tetra- or pentasubstituted by A, Ph, OH, GA, SH, SA, OPh, SPh, NH$_2$, NHA, NA$_2$, NHPh, Hal, NO$_2$, CN, (CH$_2$)$_m$COOH, (CH$_2$)$_m$COOA, (CH$_2$)$_m$CONH$_2$, (CH$_2$)$_m$CONHA, CHO, COA, S(O)$_m$A, S(O)$_m$Ph, NHCOA, NHCOPh, NHSO$_2$A, NHSO$_2$Ph, or SO$_2$NH$_2$,
Ph is phenyl which is unsubstituted or mono-, di- or trisubstituted by A, Hal, CN, COOR, COOH, NH$_2$, NO$_2$, OH or OA,
A is alkyl having 1 to 10 C atoms wherein 1-7 H atoms are each optionally replaced by F and/or chlorine,
Hal is F,Cl, Br or I and
m is 0, 1 or 2, or
a salt, or stereoisomer thereof, including mixtures thereof in all ratios.

5. A compound according to claim 4, wherein R$^1$ is (CH$_2$)$_m$CONH$_2$, (CH$_2$)$_m$CONHA, or (CH$_2$)$_m$CONA$_2$.

6. A compound according to claim 1, wherein said compound is N-methyl-4-{4-[5-(4-chloro-3-trifluoromethylphenylcarbamoyl)-1H-pyrrol-3-yl]phenoxy}-pyridine-2-carboxamide, or a pharmaceutically acceptable salt thereof.

7. A compound according to claim 1, wherein said compound is N-methyl-4-{3-[5-(4-chloro-3-trifluoromethylphenylcarbamoyl)-1H-pyrrol-3-yl]phenoxy}-pyridine-2-carboxamide, or a pharmaceutically acceptable salt thereof.

8. A compound according to claim 1, wherein said compound is N-methyl-4-{4-[5-(3-chloro-4-methylphenylcarbamoyl)-1H-pyrrol-3-yl]phenoxy}pyridine-2-carboxamide, or a pharmaceutically acceptable salt thereof.

9. A compound according to claim 1, wherein said compound is N-methyl-4-{4-[5-(2-methoxy-5-trifluoromethylphenylcarbamoyl)-1H-pyrrol-3-yl]phenoxy}-pyridine-2-carboxamide, or a pharmaceutically acceptable salt thereof.

10. A compound according to claim 1, wherein said compound is N-methyl-4-{3-[5-(3-chloro-4-methylphenylcarbamoyl)-1H-pyrrol-3-yl]phenoxy}pyridine-2-carboxamide, or a pharmaceutically acceptable salt thereof.

11. A compound according to claim 1, wherein said compound is N-methyl-4-{4-[5-(3-chloro-6-methoxyphenylcarbamoyl)-1H-pyrrol-3-yl]phenoxy}pyridine-2-carboxamide, or a pharmaceutically acceptable salt thereof.

12. A compound according to claim 1, wherein said compound is N-methyl-4-{3-[5-(3-chloro-6-methoxyphenylcarbamoyl)-1H-pyrrol-3-yl]phenoxy}pyridine-2-carboxamide, or a pharmaceutically acceptable salt thereof.

13. A compound according to claim 1, wherein said compound is N-methyl-4-{3-[5-(2-methoxy-5-trifluoromethylphenylcarbamoyl)-1H-pyrrol-3-yl]phenoxy}-pyridine-2-carboxamide, or a pharmaceutically acceptable salt thereof.

14. A compound according to claim 1, wherein said compound is N-methyl-4-{3-[5-(2,5-dimethoxy-4-chlorophenylcarbamoyl)-1H-pyrrol-3-yl]phenoxy}pyridine-2-carboxamide, or a pharmaceutically acceptable salt thereof.

15. A compound according to claim 1, wherein said compound is N-methyl-4-{3-[5-(4-bromo-3-trifluoromethylphenylcarbamoyl)-1H-pyrrol-3-yl]phenoxy}-pyridine-2-carboxamide, or a pharmaceutically acceptable salt thereof.

16. A compound according to claim 1, wherein said compound is N-methyl-4-{3-[5-(3-trifluoromethoxyphenylcarbamoyl)-1H-pyrrol-3-yl]phenoxy}pyridine-2-carboxamide, or a pharmaceutically acceptable salt thereof.

17. A compound according to claim 1, wherein said compound is N-methyl-4-{3-[5-(4-tert-butylphenylcarbamoyl)-1H-pyrrol-3-yl]phenoxy}pyridine-2-carboxamide, or a pharmaceutically acceptable salt thereof.

18. A compound according to claim 1, wherein said compound is N-methyl-4-{3-[5-(3,4-dichlorophenylcarbamoyl)-1H-pyrrol-3-yl]phenoxy}pyridine-2-carboxamide, or a pharmaceutically acceptable salt thereof.

19. A compound according to claim 1, wherein said compound is N-methyl-4-{3-[5-(4-chloro-3-methyl-6-methoxyphenylcarbamoyl)-1H-pyrrol-3-yl]phenoxy}-pyridine-2-carboxamide, or a pharmaceutically acceptable salt thereof.

20. A compound according to claim 1, wherein said compound is N-methyl-4-{3-[5-(2,4-dimethoxy-5-trifluoromethoxyphenylcarbamoyl)-1H-pyrrol-3-yl]-phenoxy}pyridine-2-carboxamide, or a pharmaceutically acceptable salt thereof.

21. A compound according to claim 1, wherein said compound is N-methyl-4-{3-[5-(2-dimethylamino-5-trifluoromethylphenylcarbamoyl)-1H-pyrrol-3-yl]-phenoxy}pyridine-2-carboxamide, or a pharmaceutically acceptable salt thereof.

22. A compound according to claim 1, wherein said compound is N-methyl-4-{3-[5-(2-(2-methylaminoethoxy)-5-methylphenylcarbamoyl)-1H-pyrrol-3-yl]-phenoxy}pyridine-2-carboxamide, or a pharmaceutically acceptable salt thereof.

23. A compound according to claim 1, wherein said compound is N-methyl-4-{3-[5-(2-(2-dimethylaminoethoxy)-5-methylphenylcarbamoyl)-1H-pyrrol-3-yl]-phenoxy}pyridine-2-carboxamide, or a pharmaceutically acceptable salt thereof.

24. A compound according to claim 1, wherein said compound is N-methyl-4-{3-[5-(2-[(2-dimethylaminoethyl)methylamino]-5-methylphenylcarbamoyl)-1H-pyrrol-3-yl]phenoxy}pyridine-2-carboxamide, or a pharmaceutically acceptable salt thereof.

\* \* \* \* \*

UNITED STATES PATENT AND TRADEMARK OFFICE
CERTIFICATE OF CORRECTION

PATENT NO. : 7,598,274 B2  Page 1 of 1
APPLICATION NO. : 10/579825
DATED : October 6, 2009
INVENTOR(S) : Finsinger et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 607 days.

Signed and Sealed this

Twenty-eighth Day of September, 2010

David J. Kappos
*Director of the United States Patent and Trademark Office*